US006979546B2

(12) United States Patent
Moretta et al.

(10) Patent No.: US 6,979,546 B2
(45) Date of Patent: Dec. 27, 2005

(54) TRIGGERING RECEPTOR INVOLVED IN NATURAL CYTOTOXICITY MEDIATED BY HUMAN NATURAL KILLER CELLS AND ANTIBODIES THAT IDENTIFY THE SAME

(75) Inventors: Alessandro Moretta, Genoa (IT); Cristina Bottino, Genoa (IT); Roberto Biassoni, Genoa (IT)

(73) Assignees: Universita di Genova (IT); Innate Pharma S.A.S. (FR)

( * ) Notice: Subject to any disclaimer, the term of this patent is extended or adjusted under 35 U.S.C. 154(b) by 291 days.

(21) Appl. No.: 10/036,444

(22) Filed: Jan. 7, 2002

(65) Prior Publication Data

US 2002/0142445 A1 Oct. 3, 2002

Related U.S. Application Data

(62) Division of application No. 09/440,514, filed on Nov. 15, 1999, now abandoned.

(51) Int. Cl.$^7$ ........................... G01N 33/53; C12N 5/08; C07K 16/28; C12P 21/08
(52) U.S. Cl. ...................... 435/7.1; 435/7.24; 435/395; 435/402; 530/387.1; 530/387.3; 530/388.22; 530/389.6; 530/391.1; 530/391.3; 530/809
(58) Field of Search ................................ 435/7.1, 7.24, 435/395, 402; 530/387.1, 387.3, 388.22, 389.6, 391.1, 391.3, 809, 39.1

(56) References Cited

U.S. PATENT DOCUMENTS 5,530,101 A  *  6/1996 Queen et al. ............. 530/387.3

FOREIGN PATENT DOCUMENTS

| WO | WO 95/06247 | 3/1995 |
| WO | WO 99/23867 | 5/1999 |

OTHER PUBLICATIONS

Harlow et al, in Antibodies a Laboratory Manual, 1988, Cold Spring harbor laboratory publication, Cold Spring Harbor, NY, pp. 92–94, pp. 116–117, 359–367, and 390–398.*
Campbell et al, in Monoclonal Antibody Technology, 1984, Elsevier Science Publisher, New York, NY, p. 1–32.*
Biassoni et al, Accession No. AJ223153 Sep. 1, 1999.*
Ellison et al, J. Immunological Methods 186: 233–243; 1995.*
Abaza et al, J of Protein Chemistry 11(5): 433–444, 1992.*
Ngo et al., 1994, The Protein Folding Problem and Tertiary Structure Prediction, pp. 492–495.*
Kuby et al, 1994, Immunology, Second edition, pp. 86–96.*
Nalabolu et al., 1996, Genomics 31 :215–222.
Moretta, A., Cell, 1997, Jul. 11; 90(1) :13–8.
Genbank Nov. 1997, 1C7 sequence, accession No. AF 031138.

Sivori, S. et al., J. Exp. Med. Oct. 6, 1997; 186(7) :1129–36.
Moretta, A. et al., Eur. J. Immunogenet. Dec. 1997; 24(6) :455–68.
Moretta, A., et al., Curr. Top Microbiol. Immunol. 1998; 230 :15–23.
Vitale, M., et al., J. Exp. Med. Jun. 15, 1998; 187(12) :2065–72.
Poccia, F. et al., Immunol. Today, Jun. 1998; 19(6) :253–6.
Pessino, A., et al., J. Exp. Med., Sep. 7, 1998; 188(5) :953–60.
Cantoni, C., et al., J. Exp. Med. Mar. 1, 1999; 189(5) :787–96.
Biassoni, R. et al., Eur. J. Immunol., Mar. 1999; 29(3) :1014–20.
Biassoni, R. et al., Semin. Cancer Biol., Feb. 1999; 9(1) :13–8.
Sivori, S. et al., Eur. J. Immunol., May 1999; 29(5) :1656–66.
Falco, M. et al., Immunol. Lett., Jun. 1, 1999; 68(2–3) :411–4.
Neville, M.J. and Campbell, R.D., 1999, J. Immunol. 162 :4745–4754.
Moretta, A. et al., Curr. Top. Microbiol. Imunol., 1999; 244 :69–84.
Genbank disclosure on AJ 223153 sequence.
Ngo et al, in The Protein Folding Problem and Tertiary Structure . . . , 1994, Merz et al (ed.), Birkhauser, Boston, MA, pp. 433 and 492–495.
Skolnick et al, From genes to protein structure and function: novel applications . . . , Jan. 2000, Trends in Biotech. 18(1):34–39.
Attwood et al, The babel of bioinformatics, Oct. 2000, Science 290 (5491):471–473.
Mikayama et al, Molecular cloning and functional expression of cDNA . . . , Nov. 1993, Proc. Natl. Acad. Sci., USA, vol. 90: 10056–10060.
Voet et al, Biochemistry I, 1990, pp. 126–234.
Kuby et al, 1994, Immunology, Second edition, pp. 85–96.
Colman et al, Effects of amino acid sequence changes . . . , 1994, A structural view of immune recognition by antibodies, pp. 33–36.
Nalabolu et al, Accession 014932, Jan. 1998.
Biassoni et al. "Homo sapiens mRNA for activating NK–A1 receptor" XP–002167564 EMBL Accession No. AJ223153 (1999).
Cantoni et al. "NKp44, a triggering receptor involved in tumor cells lysis by activated human natural killer cells, is a novel member of the immunoglobulin superfamily" XP–002167574 J. Exp. Med. 189:787–795 (1999).

(Continued)

Primary Examiner—Christina Chan
Assistant Examiner—Phuong Huynh
(74) Attorney, Agent, or Firm—Saliwanchik, Lloyd & Saliwanchik

(57) ABSTRACT

The invention relates to a novel compound termed NKp30 that is selectively expressed by all mature NK cells and that is involved in human natural cytotoxicity as an activatory receptor, to new antibodies that bind to the NKp30 structure, and to the pharmaceutical and medicinal uses thereof.

11 Claims, 16 Drawing Sheets

OTHER PUBLICATIONS

Nalabolu et al. "1C7 precursor" XP–002167565 SwissPROT Accession No. 014932 (1998).

Nalabolu et al. "Genes in a 220–kb region spanning the TNF cluster in human MHC" XP–002101698 Genomics 31:215–222 (1996).

Pende et al. "Identification and molecular characterization of NKp30, a novel triggering receptor involved in natural cytotoxicity mediated by human natural killer cells" XP–002167575 J. Exp. Med. 190:1505–1516 (1999).

Pessino et al, "Molecular cloning of NKp46: A novel member of the immunoglobulin superfamily involved in triggering of natural cytotoxicity" XP–000953037 J. Exp. Med. 188:953–960 (1998).

Utans et al, "Allograft inflammatory factor–1" XP–002073637 Transplantation 61:1387–1392 (1996).

International Search Report for PCT/EP00/11697 dated Jun. 25, 2001.

* cited by examiner

Cells    Daudi    NK

69 —
45 —
28 —         
18 —

Blot        AZ20

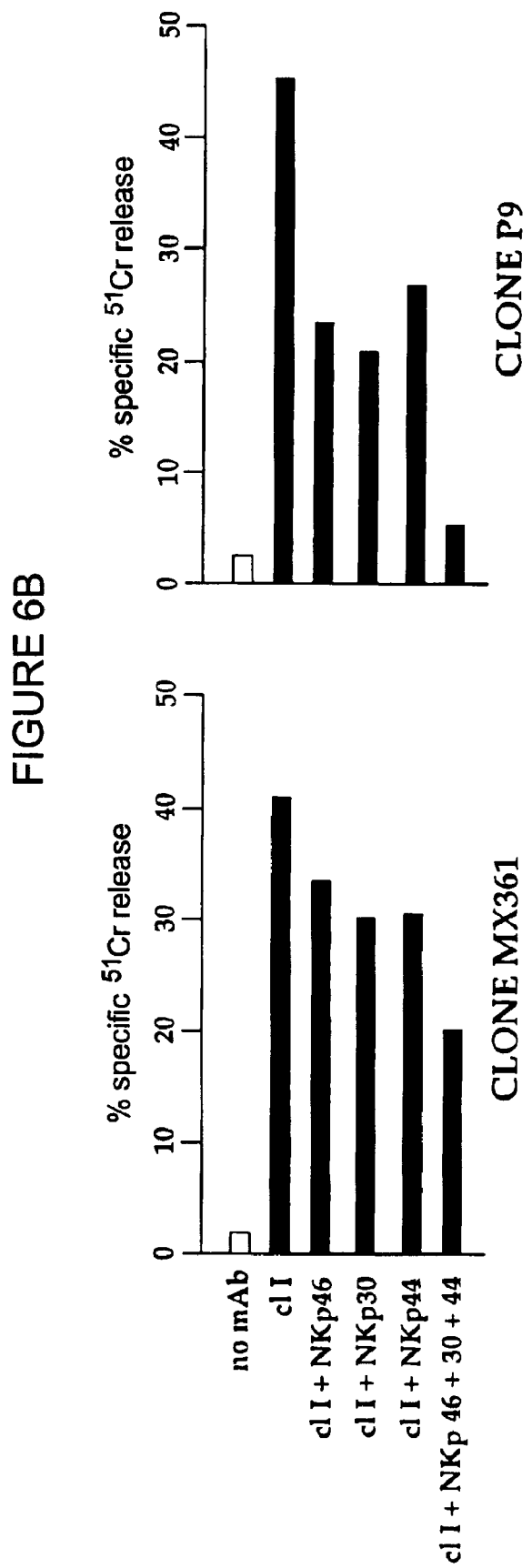

```
mawmlllili  mvhpgscalW  VSQPPEIRTL  EGSSAFLPQS  FNASQGRLAI    50
GSVTWFRDEV  VPGKEVRNGT  PEFRGRLAPL  ASSRFLHDHQ  AELHIRDVRG   100
HDASIYVQRV  EVLGLGVGTG  NGTRLVVEKE  HPQLGAGTVL  LLRAGFYAVS   150
FLSVAVGSTV  YYQGKCHCHM  GTHCHSSDGP  RGVIPEPRCP              190
```

FIGURE 7C

```
1    ccttcctcct ccacccagac ctcactgctc agatcccctt cgccaactgg gacatcttcc    60
61   gacatggcct ggatgctgtt gctcatcttg atccaggatc ctgtgctctc   120
121  tgggtgtccc agcccctga gattcgtacc ctggaaggat cctctgcctt cctgccctgc   180
181  tccttcaatg ccagccaagg gagactggcc attggctccg tcacgtgtt ccgagatgag   240
241  gtggttccag ggaaggaggt gaggaatgga accccagagt tcaggggccg cctgccccca   300
301  cttgcttctt cccgttttcct ccatgaccac caggctgagc tgcacatccg ggactgtgcga   360
361  ggccatgacg ccagcatcta cgtgtgcaga gtggaggtgc tgggcctttgg tgtcgggaca   420
421  gggaatggga ctcggctggt ggtggagaaa gaacatcctc agctagggggc tggtacagtc   480
481  ctcctcttc gggctggatt ctatgctgtc agcttttctct ctgtgccgt gggcagcacc   540
541  gtctattacc agggcaaatg ccactgtcac atgggaacac actgccactc ctcagatggg   600
601  cccgaggrg tgattccaga gcccagatgt ccctagtcct cttcaaaaga ccccaataaa   660
661  tctgccccac cact
```

TRIGGERING RECEPTOR INVOLVED IN NATURAL CYTOTOXICITY MEDIATED BY HUMAN NATURAL KILLER CELLS AND ANTIBODIES THAT IDENTIFY THE SAME

This application is a division of application Ser. No. 09/440,514, filed Nov, 15, 1999, now abandoned the entire content of which is hereby incorporated by reference in this application.

FIELD OF THE INVENTION

The invention relates to a novel compound termed NKp30 that is selectively expressed by all mature NK cells and that is involved in human natural cytotoxicity as an activatory receptor, to new antibodies that bind to the NKp30 structure, and to the pharmaceutical and medicinal uses thereof.

BACKGROUND OF THE INVENTION

Natural killer cells (NK cells) provide an efficient effector mechanism by which immunosurveillance eliminates tumor or virally infected cells. A well-defined characteristic of NK cells is their ability to lyse target cells deficient in expression of MHC class I molecules. This observation has been basic for the identification of different inhibitory receptors expressed by NK cells. Upon binding to the MHC-class I molecules expressed on target cells, these receptors deliver inhibitory signals that down-regulate cytolytic functions. In humans, recognition of HLA-class I molecules is mediated by two types of receptors: those belonging to the lg superfamily which include both KIR and LIR-1/ILT-2 proteins whose ligands are represented by various groups of HLA-A, -B and -C alleles, and the lectin-like CD94/NKG2A receptor complex which recognizes HLA-E molecules. The expression of these inhibitory receptors explains how NK cells can distinguish between HLA-deficient and normal cells. On the other hand, limited information existed in the activating NK receptors responsible for triggering the natural cytotoxicity. Only recently two distinct NK-specific receptors have been identified that play an important role in the NK cell mediated recognition and killing of HLA Class I defective target cells. These receptors, termed NKp46 and NKp44, are members of the lg superfamily. Their cross-linking induced by specific mAbs leads to a strong NK cell activation resulting in increased intracellular Ca++ levels, in triggering of cytotoxicity and lymphokine release. Importantly, mAb-mediated masking of NKp46 and/or NKp44 resulted in inhibition of NK cytotoxicity against most, but not all, target cells. These findings, while providing evidence for a central role of NKp46 and NKp44 in natural cytotoxicity, also implied the existence of additional receptors.

SUMMARY OF THE INVENTION

It is an object of the present invention to identify a novel triggering receptor involved in NK cell mediated recognition and killing of target cells. This novel receptor of approximately 30-kD on SDS-PAGE has been termed NKp30, and is member of the lg superfamily characterized by a single V-type domain, a charged residue in the transmembrane portion, and the absence of ITAM motif in the cytoplasmic tail. Searching EMBL/Genbank/DDBJ databases revealed that the cloned NKp30 cDNA is identical to a previously identified alternatively spliced form of the 1C7 gene (available under accession no. AF031138). To date, however, owing to the lack of specific mAb, neither the function nor the surface distribution of the putative product of the 1C7 gene could be identified. NKp30 is selectively expressed on the surface of human mature NK cells, and associates with the CD3ζ signal transducing peptides that become tyrosine phosphorylated upon cell activation. NKp30 can cooperate with Nkp46 and/or Nkp44 in the induction of NK-mediated cytotoxicity against the majority of target cells, whereas it represents the major triggering receptor in the killing of certain tumors (e.g. human melanoma of the MEL 15 type).

It is another object of the invention to provide antibodies that selectively bind to NKp30 structures. Antibody-mediated crosslinking of NKp30 induces strong NK cell activation, whereas antibody-mediated NKp30 masking inhibits NK natural cytotoxicity.

The present invention thus provides useful tools for NK cell positive purification, and for NK cell natural cytotoxicity regulation. Tools according to the invention are of particular interest for regulating allogenic graft/host or transplant/host reactions (Graft or transplant improvement, Graft versus Host GvH, but also Graft versus Tumor GvT or Graft versus Leukemia GvL), and for regulating the growth of pathological cells such as tumor cells, microorganism-infected or virus-infected cells.

DETAILED DESCRIPTION OF THE INVENTION

The present invention relates to any isolated compound comprising at least one amino acid amino acid (aa) sequence that is at least 80% identical over its entire length to an amino acid sequence chosen among the group consisting of the SEQ ID NO: 2, SEQ ID NO: 4, SEQ ID NO: 5, SEQ ID NO: 6, the amino acid sequences of any immunogenic fragment thereof, and the SEQ ID NO: 7 sequence.

Among these compounds, those comprising at least one amino acid sequence that is at least 90% identical over its entire length to a amino acid sequence chosen among said group are preferred and those for which said identity is of at least 95% are especially preferred. Furthermore, those for which said identity is of at least 97% are highly preferred, and among these those for which said identity is of at least 98% and at least 99% are particularly highly preferred, with those for which it is of at least 99% being the more preferred.

"Identity", as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in *Computational Molecular Biology*, Lesk, A. M., ed., Oxford University Press, New York, 1988. Methods to determine identity are designed to give the largest match between the sequences tested. Moreover, methods to determine identity are codified in publicly available computer programs, such as the GAP program in the GCG program package (Devereux, J., et al., *Nucleic Acids Research* 12(1): 387(1984)), BLAST, BLASTN (Altschul, S. F. et al., *J. Molec. Biol.* 215: 403–410 (1990), and FASTA (Pearson and Lipman Proc. Natl. Acad. Sci. USA 85; 2444–2448 (1988)).

The SEQ ID NO: 2 relates to the human NKp30 190aa polypeptide (about 30-kD on SDS-PAGE), (which is selectively expressed by NK cells, and particularly mature NK cells, the SEQ ID NO: 4 to the extracellular region of human NKp30 receptor, the SEQ ID NO: 5 to the transmembrane region of human NKp30 receptor, the SEQ ID NO: 6 to the cytoplasmic tail of the human NKp30 receptor, the SEQ ID NO: 7 to a 15 aa immunogenic peptide derived from SEQ ID NO: 2. The present invention also includes variants of the aforementioned polypeptides, that is polypeptides that vary from the referents by conservative amino acids substitutions, whereby a residue is substituted by another with like characteristics. Typical such substitutions are among Ala, Val, Leu and lle; among Ser and Thr; among the acidic residues Asp and Glu; among Asn and Gln; and among the basic residues Lys and Arg; or aromatic residues Phe and Tyr. These compounds will be herein referred to as the "aa compounds of the invention".

It also provides with isolated compounds comprising at least one amino acid sequence chosen among the group consisting of the SEQ ID NO: 2, SEQ ID NO: 4, SEQ ID NO: 5, SEQ ID NO: 6, the amino acid sequences of any immunogenic fragment thereof, and the SEQ ID NO: 7 sequence, and also comprising at least one CD3ζ chain.

By "immunogenic fragment", it is herein meant any polypeptidic or peptidic fragment which is capable eliciting an immune response such as (i) the generation of antibodies binding said fragment and/or binding any form of the NKp30 molecule comprising said fragment, including the membrane receptor and mutants derived therefrom, (ii) the stimulation of a T-cell response involving T-cells reacting to the bi-molecular complex comprising any MHC molecule and a peptide derived from said fragment, (iii) the binding of transfected vehicles such as bacteriophages or bacteria expressing genes encoding mammal immunoglobulins. Alternatively, an immunogenic fragment also refers to any construction capable to elicit an immune response as defined above, such as a peptidic fragment conjugated to a carrier protein by covalent coupling, a chimeric recombinant polypeptide construct comprising said peptidic fragment in its aa sequence, and specifically includes cells transfected with a cDNA of which sequence comprises a portion encoding said fragment.

The present invention also relates to any isolated compound comprising at least one polynucleotidic sequence that is at least 80% identical over its entire length to a polynucleotide sequence chosen among the group consisting of the SEQ ID NO: 1, SEQ ID NO: 10, SEQ ID NO: 12, SEQ ID NO: 13 polynucleotidic sequences, and the polynucleotidic sequences which encode according to the universal genetic code, and taking into account its redundancy, the SEQ ID NO: 2, SEQ ID NO: 4, SEQ ID NO: 5, SEQ ID NO: 6 sequences, the amino acid sequences of any immunogenic fragment of SEQ ID NO: 2, SEQ ID NO: 4, SEQ ID NO: 5 and SEQ ID NO: 6 sequences, and the SEQ ID NO: 17 sequence. Among these compounds, those comprising at least one polynucleotidic sequence that is at least 90% identical over its entire length to a polynucleotidic sequence chosen among said group are preferred and those for which said identity is of at least 95% are especially preferred. Furthermore, those for which said identity is of at least 97% are highly preferred, and among these those for which identity is of at least 98% and at least 99% are particularly highly preferred, with those for which it is of at least 99% being the more preferred. Preferred embodiments are isolated compounds comprising at least one polynucleotidic sequence encoding a polypeptide that retain substantially the same biological function or activity as the mature polypeptide encoded by a DNA of SEQ ID NO: 1, SEQ ID NO: 10, SEQ ID NO: 12, SEQ ID NO: 13. In accordance with certain preferred embodiments of this invention, there are provided compounds comprising at least one polynucleotide that hybridizes, particularly under stringent conditions, to said isolated compounds. Such hybridizing polynucleotides notably include the group of polynucleotides complementary to those of SEQ ID NO: 1, SEQ ID NO: 10, SEQ ID NO: 12, SEQ ID NO: 13. A specific example of stringent hybridization conditions is overnight incubation at 42° C. in a solution comprising: 50% formamide, 5x SSC (150 mM NaCl, 15 mM trisodium citrate), 50 mM sodium phosphate (pH7.6), 5x Denhardt's solution, 10% dextran sulfate, and 20 micrograms/ml of denatured, sheared salmon sperm DNA, followed by washing the hybridization support in 0.1xSSC at about 65° C. Hybridization and wash conditions are well known and exemplified in Sambrook, et al., *Molecular Cloning: A Laboratory Manual,* Second Edition, Cold Spring Harbor, N.Y., (1989), particularly Chapter 11 therein. Solution hybridization may also be used with the polynucleotide sequences provided by the invention. The present invention also encompasses NKp30 variants expressed in any mammalian species other than the human species, notably in monkey, rat, mouse, dog, cow, and rabbit. Indeed such variants appeal highly conserved among species. It also encompasses NKp30 non functional mutants such as point mutants of the transmembrane domain in which R residue is replaced by an uncharged residue such as A. These compounds will be herein referred to as the "pln compounds of the invention".

The SEQ ID NO: 1 relates to the human NKp30 cDNA (mRNA of about 1 kb), the SEQ ID NO: 10 to a NKp30 cDNA probe of 421 bp (position 57 to position 477 of SEQ ID NO: 1), the SEQ ID NO: 12 to a NKp30 cDNA amplification product of 606 bp (from position 57 to position 662 on SEQ ID NO: 1), the SEQ ID NO: 13 to NKp30 coding sequence from position 64 to position 636 on SEQ ID NO: 1. Polynucleotides are herein meant as also including oligonucleotides, and correspond to any polynucleotidic nature, including DNA, genomic DNA, RNA, tRNA, mRNA, and cDNA. The present invention thus also provides with transfection vectors carrying at least one isolated compound chosen among the group consisting of said polynucleotidic products, and with a cell transfected by at least one of such isolated compound or by at least one of such vectors.

The invention also relates to polynucleotidic compounds chosen among the group consisting of the (SEQ ID NO. 8; SEQ ID NO: 9) couple, the (SEQ ID NO: 8; SEQ ID NO: 11) couple, the SEQ ID NO: 10 polynucleotide, the SEQ ID NO: 12 polynucleotide.

Such compounds are notably useful for NKp30 detection in a sample. Couples such as the (SEQ ID NO: 8; SEQ ID NO: 9) and the (SEQ ID NO: 8; SEQ ID NO: 11) can e.g. be used as up and down PCR primer couple. Polynucleotides such as the SEQ NO: 10 and the SEQ ID NO: 12 polynucleotides can be used as NKp30 probes. The SEQ ID NO: 10 sequence corresponds to a 421 bp cDNA derived from SEQ ID NO: 1 probe (from position 57 to position 477 on SEQ ID NO: 1); it can e.g. be used as an NKp30 probe which allows to identify and isolate the NKp30 gene in a biological sample. This NKp30 gene beside appears as highly conserved among mammalian species. The SEQ ID NO: 12 corresponds to 606 bp cDNA derived from SEQ ID NO: 1 (from position 57 to position 662 on SEQ ID NO: 1); it corresponds to the product obtained via PCR amplification with the SEQ ID NO: 8 and SEQ ID NO: 11 primer couple.

In a further aspect, the invention provides with a composition of the antiserum type which is such as obtained by immunizing a mammalian with at least one isolated aa compound of the invention, this at least one aa compound being optionally coupled to an immunogenicity enhancer, and collecting the antiserum thus produced.

It thus also provides with:
isolated compounds which can recognize in a reaction of the antibody-antigen type at least one isolated aa compound of the invention, and with
isolated antibodies, and particularly isolated monoclonal antibodies directed against at least one aa compound of the invention.

In another aspect, the invention relates to isolated immuno-reactive fragments of any antibody chosen among the group consisting of the isolated antibodies and monoclonal antibodies according to the invention, such fragments notably include Fab, F(ab')2, and CDR antibody fragments. The skilled person will note that humanized antibodies of the invention can be derived therefrom as desired, notably when intended to be administered to a human person. By "immuno-reactive fragments of an anubody", it is herein meant any antibody fragment comprising the antigen binding-site. Such fragments thus include F(ab')2 fragments obtained either by enzymatic digestion of said antibody by proteolytic enzymes such as pepsin or papain, and Fab fragments derived thereof by reduction of the sulfhydryl groups located in the hinge regions, as known by any skilled person. Immunoreactive fragments can also comprise recombinant single chain or dimeric polypeptides whose sequence comprises the CDR regions of the antibody of interest.

The invention more particularly relates to any isolated antibody that is directed against at least one aa compound of the invention and that does not bind to any T cell surface molecule, nor to any B cell surface molecule. Preferred antibodies do no bind monocytes, granulocytes, and preferably do not bind any nucleated cell from peripheral blood except NK cells. Most preferred isolated antibodies do neither bind any NKp46 or NKp44 extracellular portion, nor any other NK cell surface molecule.

Such binding reactions are herein meant as binding reactions such as observed in reactions of the antibody-antigen type under experimental conditions appropriate for such antibody-antigen type recognition reactions.

Such binding reactions can be achieved e.g. by contacting a leucocyte suspension from peripheral blood with the antibody, detecting the immune complexes thus formed e.g. by contacting with a secondary anti-immunoglobulin reagent carrying a fluorescent label, and enumerating and identifying cells binding the antibody using a flow cytometer such as Beckman-Coulter XL. The identification of the various leucocyte subsets in this experiment is based on size and optical properties of the various cell subsets. Alternatively, after being contacted with the antibody of interest as described above, the same leucocyte suspension can be contacted with a fluorochrome-conjugated antibody binding specifically to a leucocyte subset such as CD3 antibody UCHT-1 which binds specifically to T-cells, thus allowing a phenotypic definition of the leucocyte subset binding the antibody of interest. Several experiments of dual labeling as described can be performed, using a panel of subset-specific antibodies, to further delineate the cellular reactivity of the antibody of interest.

Preferred antibodies of the invention can induce a statistically significant ($p<0.05$) increase in NK cell activation as assessed by (i) natural cytotoxicity towards MHC class I negative targets, tumor cells, virally-infected cells, allogeneic cells, (ii) cytotoxicity towards antibody-coated target cells, (iii) increases in intracytoplasmic Ca2+ concentration, (iv) induction of tyrosine phosphorylation of intracytoplasmic adaptor/effector molecules such as ZAP70, Syk, LAT, SLP76, Shc, Grb2, phospholipase C-gamma enzymes, phosphatidyl-inositol 3-kinases, (v) phosphorylation of receptor-associated transducing chains KARAP/DAP12 or CD3zeta or FcRgamma, (vi) cytokine secretion such as interferon gamma, tumor necrosis factors, IL5, IL10, chemokines (such as MIP-1 alpha), TGFbeta, (vii) up- or down-regulation of NK cell surface molecules, such as CD69 and PEN5 respectively.

Examples of preferred isolated antibodies of the invention include isolated antibodies that are directed against at least one isolated aa compound of the invention, and that can induce an increase of at least about 4, preferably at least about 5, more preferably at least about 6 times, in the natural cytotoxicity triggered by a NK cell placed in the presence of a target cell in a 1:1 ratio.

Most preferred isolated antibodies of the invention are directed against at least one isolated aa compound of the invention, do not bind to any T or B cell surface molecule, and can induce an increase of at least about 4, preferably at least about 5, more preferably at least about 6 times, in the natural cytotoxicity triggered by a NK cell placed in the presence of a target cell in a 1:1 ratio.

Any isolated antibody of the invention can be coupled to any appropriate label for visualisation purposes. Such labels include e.g. the fluorescent labels, the radioactive labels, and the enzymatic labels.

In another aspect, the present invention relates to any solid support on which is attached at least one isolated antibody that is directed against at least one isolated aa compound of the invention. Any solid support allowing said attachment is appropriate. Particularly appropriate solid supports include paramagnetic microspheres that can be used as an affinity matrix such as Dynabeads® from Dynal a.s. (Olso, Norway), submicroscopic MACS microbeads from Miltenyi Biotec gmbh (Gladbach, Germany), semi-permeable substrate consisting of an array of hollow fibers as described in U.S. Pat. No. 5,763,194, dense particles allowing separation by sedimentation as described in U.S. Pat. No. 5,576,185.

An advantageous embodiment of these solid supports of the invention comprises the presence, on said supports, of anti-NKp46 and/or anti-NKp44 antibodies, or immunogenic fragments or derivatives thereof further attached on said solid support. As illustrated below, the NKp30 receptor of the invention can indeed cooperate in additional or synergetic way with other receptors such as the NKp46 and/or NKp44 receptors.

The present invention also relates to any hybridoma that produces a monoclonal antibody that is directed against at least one isolated aa compound of the invention. Monoclonal antibodies of the invention can be prepared using any technique that provides for the production of antibody molecules by continuous cell lines in culture. These include, but are not limited to, the original techniques of Köhler and Milstein, *Nature,* 265:495–497 (1975), modified as described in Anderson et al.,*J. Immunol.,*143:1899 (1989), the content of which is hereby incorporated by reference.

Screening procedures that can be used to screen hybridoma cells producing antibodies to NKp30 includes, but are not limited to, (1) enzyme-linked immunoadsorbent assays (ELISA), (2) immunoprecipitation and (3) fluorescent activated cell sorting (FACS) analyses. Many different ELISAS that can be used to screen for the anti-NKp30 monoclonal antibodies can be envisioned by persons skilled in the art.

Initial screening is preferably conducted by screening hybridoma supernatants by flow cytometry for their reactivity with NK cells, but not with T cells, and monocytes. Further characterization of the hybridomas can be conducted by testing on purified populations of lymphoid and non-lymphoid cells by indirect immunofluorescence assays and flow cytometry, substantially as described in the Examples herein. Monoclonal antibodies that recognize an NKp30 epitope will react with an epitope that is present on a high percentage NK cells e.g., at least about 70–90%, preferably about 80%, of such cells, but will not significantly react with $CD3^+$ T cells or $CD20^+$ B cells. In preferred embodiments, the antibody will also be unreactive with monocytes, granulocytes, platelets, and red blood cells.

Monoclonal antibodies that compete with such antibodies in competition assays well known to persons skilled in the art are likely to recognize essentially the same epitopes.

One the desired hybridoma has been selected and cloned, the resultant antibody may be produced in one of two major ways. The purest monoclonal antibody is produced by *in vitro* culturing of the desired hybridoma in a suitable medium for a suitable length of time, followed by the recovery of the desired antibody from the supernatant. The length of time and medium are known or can readily be determined. This *in vitro* technique produces essentially monospecific monoclonal antibody, essentially free from other species of anti-human immunoglobulin. However, the in vitro method may not produce a sufficient quantity or concentration of antibody for some purposes, since the quantity of antibody generated is only about 50 µg/ml.

To produce a much larger quantity of monoclonal antibody, the desired hybridoma may be injected into an animal, such as a mouse.

Preferably the mice are syngeneic or semi-syngeneic to the strain from which the monoclonal-antibody producing hybridomas were obtained. Injection of the hybridoma causes formation of antibody producing tumors after a suitable incubation time, which will result in a high concentration of the desired antibody (about 5–20 mg/ml) in the ascites of the host animal.

Antibody molecules can be purified by known techniques e.g. by immunoabsorption or immunoaffinity chromatography, chromatographic methods such as high performance liquid chromatography or a combination thereof.

Following these protocols, any person skilled in this area of technology can readily isolate hybridomas that produce monoclonal antibodies exhibiting specificity for NKp30. It is thus contemplated that the present invention encompasses all monoclonal antibodies exhibiting the desired anti-NLp30 characteristics.

In a further aspect, the invention relates to any composition of the anti-antiserum type which is such as obtained by immunizing a mammalian with at least one substance chosen among the group consisting of the compositions of the antiserum-type according to the invention, the isolated antibody-antigen type compounds of the invention, the antibodies and monoclonal antibodies of the invention, this at least one substance being optionally coupled to an immunogenicity enhancer, and collecting the anti-antiserum thus produced. It also relates to isolated anti-antibodies and monoclonal anti-antibodies which can recognize in a reaction of the antibody-antigen type at least one isolated aa compound of the invention, and to pharmaceutical compositions comprising the same.

The products of the invention can be used in a variety of ways. Advantageous ways include the medicinal applications thereof. NKp30 is selectively expressed by all NK cells, both freshly isolated and cultured in the presence of one, two or multiple cytokines such as IL-2, IL-12, IL-15, FLT-3 ligand, SCF, thus representing an optimal marker for NK cell identification. The present invention notably allows the skilled person to perform a method for detecting or quantifying the presence of NK cells in a biological sample, the detection or quantification of the NKp30 molecules on and/or in said NK cells. The methods of the invention notably comprise:

contacting the biological sample with at least one object chosen among the group consisting of the antiserum-type compositions of the invention, the isolated antibody-antigen type compounds according to the present invention, the isolated antibodies of the invention, the isolated immuno-reactive fragments, the solid supports, and the hydridomas of the invention under conditions appropriate for immune complex formation, and detecting or quantifying the immune complexes thus formed, or comprising contacting the biological sample with at least one product chosen among the group consisting of the isolated pin compounds of the invention, the polynucleotidic couples of the invention such as (SEQ ID NO: 8; SEQ ID NO: 9), (SEQ ID NO: 8; SEQ ID NO: 11), the isolated polynucleotides comprising the SEQ ID NO: 10 and/or NO:12 according to the invention, under conditions appropriate for the formation of polynucleotide hybridization products, and detecting or quantifying the hybridization products thus formed.

The present invention also allows the skilled person to perform a method for the selective removal of NK cells for a biological sample which comprises the selective removal of those cells that are $NKp30^+$. Such a method notably comprises:

contacting the biological sample with a least one object chosen among the group consisting of the antiserum-type compositions of the invention, the isolated antibody-antigen type compounds of the invention, the isolated antibodies of the invention, the isolated immuno-reactive fragments, the solid supports, and the hydridomas according to the invention, under contacting conditions appropriate for immune complex formation, and removing the cells carrying the immune complex thus formed (positive cells) from those which do not carry such complex (negative cells).

The present invention also allows the skilled person to perform a method for the positive and selective purification of NK cells from a biological sample, which comprises the positive and selective purification of those cells which are $NKp30^+$. Such a method notably comprises:

contacting the biological sample with at least one object chosen among the group consisting of the antiserum-type compositions of the invention, the isolated antibody-antigen type compounds of the invention, the isolated antibodies of the invention, the isolated immuno-reactive fragments, the solid supports, and the hydridomas according to the invention under contacting conditions appropriate for immune complex formation, and removing those cells onto which an immune complex has formed. Convenient ways for recovering the cells are well known to the skilled person. These notably include (i) mechanical disruption of the link between the cells and the object with which the positive cells have formed an immune complex, (ii) enzymatic attack of the object with which the positive cells have formed an immune complex (e.g. with papain as described in U.S. Pat. No. 5,081,030), and (iii) contacting the immune complex with an excess amount of a soluble molecule able to compete with the antibody included in the immune complex for binding with the positive cells, resulting in the disruption of the immune complex, as described for instance for the recovery of CD34+ cells in U.S. Pat. No. 5,968,753.

The invention thus also relates to any kit for detecting, quantifying, removing and/or positively purifying NK cells from a biological sample comprising said at least one object, said object being enclosed in a container.

For implementing the above-cited methods, appropriate biological samples include peripheral blood, plasma, bone marrow aspirates, lymphoid tissues, as well as cells isolated from cytapheresis, plasmapheresis and collection fluids such a synovial, cerebro-spinal, broncho-alveolar and peritoneal fluids.

In a particularly advantageous aspect, the present invention relates to a method for stimulating NK cell cytotoxicity, comprising:

contacting said NK cells under physiological conditions with at least one product chosen among the group consisting of the antiserum-type compositions according to the invention, the isolated antibody-antigen type compounds according to the invention, the isolated antibodies, the solid supports, and the hybridomas according to the invention. Said contacting is performed so as to allow NKp30 cross-linking on said NK cells. A preferred embodiment includes contacting said NK cells under physiological conditions with at least one solid support of the invention onto which anti-NKp30 antibodies are immobilized using saturating concentrations of purified antibody. NK receptor cross-linking indeed induces NK cell activity stimulation. When it is desired to achieve a net NK cell activity regulation balance in favor of stimulation, the skilled person will thus choose conditions significantly favoring NKp30 cross-linking. Such conditions notably include the use of compounds of which nature allows such a cross-linking. The products listed in the above group correspond to examples of such compounds, or allow construction thereof. Such conditions can also include the use of such cross-linking compounds in such quantities, and notably in such a density (e.g. saturating concentration) that said regulation more strongly balances in favor of NK cell cytotoxicity stimulation.

The stimulating method of the invention does advantageous not require the conventional steps of NK cell incubation in interleukines such as IL-2, IL-12, IL-15. These steps are however of course not precluded: the skilled person nevertheless can as desired choose to add these conventional steps to the method of the invention. The present invention also relates to any kit for stimulating NK cell cytotoxicity, comprising at least one of said products enclosed in a container.

For detection, quantification, removal, positive purification, and/or NK cell cytotoxicity stimulation, said methods of the invention can further comprise contacting said biological sample, or said NK cells with an anti-NKp46 or anti-NKp44 antibodies; and said kits can further comprise anti-NKp46 or anti-p44 antibodies.

Advantageously, the purifying method of the invention can simultaneously perform NK cell activation, and vice versa. This simultaneous NK cell positive purification and NK cell cytotoxicity stimulation embodiment of the invention is of particular interest when applied to biological samples, and particularly to samples deriving from human person(s) and meant to be re-administered to a human patient after treatment.

Alternatively, the present invention also provides with a method for inhibiting NK cell cytotoxicity, comprising contacting said NK cells under physiological conditions with at least one compound:

(a) capable of inhibiting the binding of NKp30 natural ligands to NKp30 receptors expressed on said NK cells, e.g. by masking NKp30 binding sites, and/or capable of inhibiting the cross-linking of the NKp30 receptors expressed by said NK cells, and/or (b) capable of inhibiting the interactions between the NKp30 molecules expressed by said NK cells, and their transduction elements, notably CD3ζ. Compounds according to (a) notably comprise the immuno-reactive fragments of the invention. Soluble NKp30 mAb of various isotypes, (IgM and preferably IgG) or immunoreactive divalent or monovalent fragments thereof can be used at saturating concentration corresponding to a 10 fold excess to their respective dissociation constant to mask NKp30 expressed on NK cells.

Compounds according to (b) notably comprise compounds capable of inhibiting the interactions between the NKp30 transmembrane charged amino acid (amino acid R at position 143 on SEQ ID NO: 1) and said transduction elements. Such (b) compounds can notably correspond to a liposoluble molecule capable under physiological conditions of binding to NKp30 transmembrane region (position 138 to 157 of SEQ ID NO: 1) so as to inhibit or block the functionalities (binding to CD3ζ) of said charged transmembrane amino acid (R at position 143). By physiological conditions, it is herein meant in vivo conditions, or *in vitro* conditions mimicking the *in vivo* ones.

The methods of the invention for the detection/quantification/selective/removal/positive and selective purification of NK cells from a biological sample, and for stimulating NK cell cytotoxicity can further comprise the contacting of said sample, or respectively NK cells, with compounds capable in said conditions of stimulating the activity of other NK receptors other NK receptor other than NKp30, and that can function in addition to, or in synergy with NKp30, e.g. the NKp46 and/or NKp44 receptors. Stimulation can be achieved, e.g. by the use of compounds capable in said conditions of cross-linking said other NK receptors, notably NKp46 and/or NKp44.

The converse of course applies to the method for inhibiting NK cell cytotoxicity according to the invention, e.g. the inhibiting method of the invention can further comprise the use of compounds capable of inhibiting the activity of said other NK receptors, e.g. by ligand binding inhibition and/or transduction/effector element binding inhibition.

A very useful aspect of the invention corresponds to a new grafting method comprising contacting an organism chosen among the group consisting of a cell to be grafted, a tissue to be grafted, an organ to be grafted, and the host organism with at least one product chosen among the group consisting of:

the antiserum-type compositions according to the invention, the isolated antibody-antigen type compounds according to the invention, the isolated antibodies, solid supports, hybridomas according to the invention, the NK cells purified from the graft donor via the purification method of the invention, the NK cells of which cytotoxicity has been stimulated via the stimulation method of the invention.

"Graft" is herein meant as also encompassing "transplant".

Said host organism can be any mammalian, including a human being.

This new grafting method is particularly useful for allogeneic grafting, and can e.g. be applied for bone marrow/stem cell grafting. It is also of particular interest for GvH inhibition, or GvT and in particular GvL stimulation. The essence of the new grafting method of the invention is to provide the patient with NK cells that have been purified from said graft, and that have been activated according to the methods and kits of the invention. This notably applies to MHC- matched or -mismatched hematopoietic grafts (bone marrow/peripheral stem cells). These activated allogeneic NK cells can e.g. be intravenously infused into the patient to be grafted, and preferably in a time window closed to the infusion of the graft: at the same time and up to about 2 days later. Amounts of activated NK cells and frequency of infusion into patients depends upon the pathology.

The new grafting method of the invention is also of particular interest in anti-tumor and/or anti-infection treatment, prevention, or palliation. In these cases, autologous NK cells from patients suffering from solid or liquid tumors, or from a viral or other micro-organism infection, that have been purified and activated according to the methods and kits of the invention can be "armed" towards the particular tumor and/or infection, e.g. by incubating said NK cells in the presence of a saturating concentration of mAb reactive towards said tumor and/or infection agent. The purified, activated, and "armed" NK cells according to the invention can then be injected intravenously into patients. Amounts of "armed" NK cells and frequency of infusion into patients depends upon the pathology.

These new grafting methods of the invention thus constitute novel NK cell-based immunotherapy based on NK cell activation via NKp30 triggering. The methods of the invention can further comprise the co-activation of other receptors which can function in addition to or in synergy with NKp30 such as NKp46 and/or NKp44 via NKp46 and/or NKp44 cross-linking compounds.

The present invention thus encompasses the use of said product for the production of a pharmaceutical composition intended for grafting enhancement, GvH inhibition, GvT and in particular GvL stimulation, and/or for the prevention, palliation, and/or therapy of solid or liquid tumors and/or of microorganism infection, notably viral infection.

The invention teaching also the skilled person to produce a pharmaceutical composition comprising at least one product chosen among the group consisting of:

the antiserum-type compositions according to the invention, the isolated antibody-antigen type compounds according to the invention, the isolated antibodies, solid supports, and hybridomas according to the invention, the isolated NK cells purified from the graft donor via the purification method of the invention, the isolated NK cells of which cytotoxicity has been stimulated via the stimulation method of the invention, together with a pharmaceutically acceptable vehicle.

Such compositions of the invention can advantageously further comprise anti-NKp46 and/or anti-NKp44 antibodies, or immunogenic fragments or derivates thereof. A variety of pharmaceutically acceptable vehicles are available to the skilled person; the choice of an appropriate one mainly depends on the galenic form and on the administration route desired. The word "pharmaceutical compositions" thus herein means any galenic form such as tablet, powder, pastes, patches, granules, microgranules, nanoparticles, colloid solution, aqueous solution, injectable solutions, sprays, liposomes. The route of administration for the in vivo therapeutic modalities may include intradermal, intramuscular, intraperitoneal, intravenous, or subcutaneous injection, intranasal route and the chirurgical route. The galenic form may also correspond to slow and/or controlled release forms.

Said at least one product has to be properly formulated so as to be tolerated and effective for the patient to which said composition will be administered. Such proper formulations are well-known by the skilled person; when the patient is a human being, these e.g. include the humanization or chimeric mimetics of said product. It may also include a pharmaceutically acceptable vehicle of which solubility and/or chemical and/or galenic properties are adapted to the desired administration route and the aimed efficiency level. Such vehicles may e.g. include saline or dextrose solutions. The composition of the invention may also further comprise any buffer, and/or any stabilizing compound that the skilled person would find appropriate to the case.

The effective dose of said at least one product will be a function of the particular product employed, the presence and nature of additional or synergetic therapeutic reagent(s) (e.g. anti-NKp46 and/or anti-NKp44 antibodies, or fragments or derivates thereof) of the patient, and of his or her clinical condition. An effective dose typically ranges from 1 ng to 100 mg/kg body weight.

Such pharmaceutical compositions can e.g. be intended for grafting/transplanting improvement for anti-tumoral prevention, palliation, therapy, such as melanoma, hepatocarcinoma, lung adenocarcinoma prevention, palliation, therapy, for anti-microbial prevention, palliation, therapy, such as anti-viral prevention, palliation, therapy. By "palliation", it is herein meant any biological result that corresponds to an improvement of the patient health; this notably includes any slowing down of the growth of the pathological cells.

In an advantageous aspect, the pharmaceutical composition of the invention allows a targeted NK cytotoxicity. Such a composition comprises at least one product chosen among the group consisting of:

the antiserum-type compositions according to the invention, the isolated antibody-antigen type compounds according to the invention, the isolated antibodies, solid supports, and hybridomas according to the invention, the isolated NK cells purified from the graft donor via the purification method of the invention, the isolated NK cells of which cytotoxicity has been stimulated via the stimulation method of the invention, said product being directly or indirectly linked to a substance capable of binding under physiological conditions to the desired target, together with a pharmaceutically acceptable vehicle. Examples of said targeting substance include anti-tumor antibodies, anti-microorganism antibodies, anti-viral antibodies, and functional equivalents thereof. Such a pharmaceutical composition for targeted NK cytotoxicity is more particularly intended for anti-tumoral prevention, palliation, therapy (e.g. melanomas, hepatocarcinoma, or lung adenocarcinoma), and for anti-microbial prevention, palliation, therapy.

The present invention also provides a method for identifying the NKp30 natural ligands. This method comprises the use of the antibodies, the antibody fragments, or the solid supports according to the invention on NK cells. The present invention thus allows the screening of chemical and/or biological library for mimetics and/or antagonists to NKp30 natural ligands.

The antibodies, the antibody fragments, or the solid supports according to the invention also allow the assessment of the level of surface NKp30 ligand expressed by a NK-susceptible target cell, and the comparison this measured level to the standard physiological one. This assessment is of special interest for the diagnostic of tumor cells and/or microorganism-infected cells, and prescription of appropriate prevention, palliation, therapy tools.

These and other features and advantages of the invention will be further apparent from the following examples. These examples are given for illustrative purposes only, and are in no way intended to restrict the scope of the present invention. Alternative embodiments, intended by any skilled person, are encompassed by the present invention.

DESCRIPTION OF THE DRAWINGS

In these examples, reference is made to FIGS. 1A to 9B (19 drawing sheets).

Figure 1A:
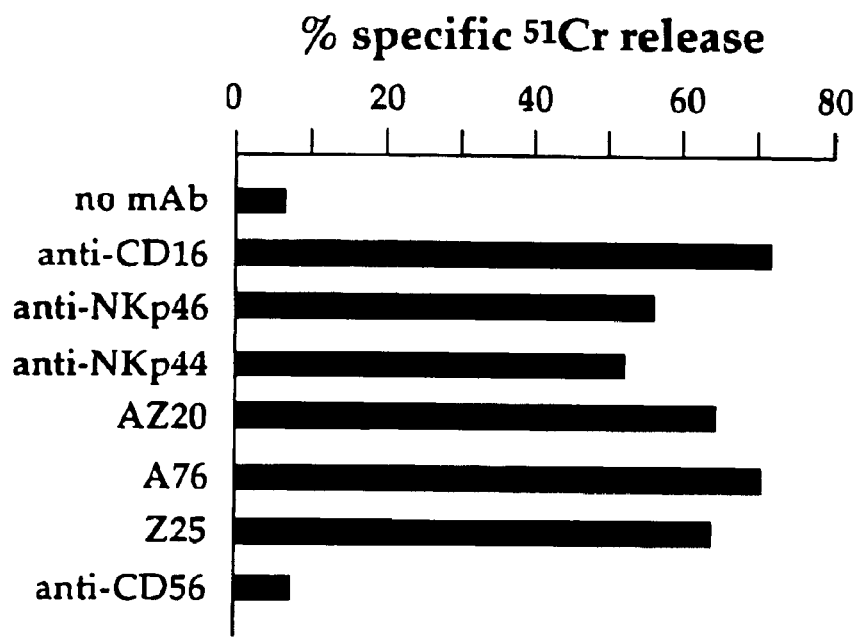
FIGS. 1A, 1B, 1C illustrate the triggering of NK-mediated cytolytic activity induced by three mAbs according to the invention (anti-NKp30 mAbs).

On FIG. 1A, a representative polyclonal NK cell population was analyzed (% specific $^{51}$Cr release) for cytolytic activity in a redirected killing assay against the Fcy R-positive P815 target cell in the absence or in the presence of c127 (anti-CD16), BAB281 (anti-NKp46), Z231 (anti-NKp44), AZ20, A76, Z25 (anti-NKp30 mAbs) and c218 (anti-CD56) mAbs. The E/T (effector:target) ratio used was 1:1. The AZ20 hybridoma (CNCM Registration Number I-2576) has been accepted for deposit at the Collection Nationale De Cultures De Micro-organismes (CNCM) Institute Pasteur, 28, rue du Dr. Roux, 757 Paris Cèdex 15, France on November 8, 2000 under the Budapest Treaty on the International Recognition of the Deposit of Microorganisms.

Figure 1B:
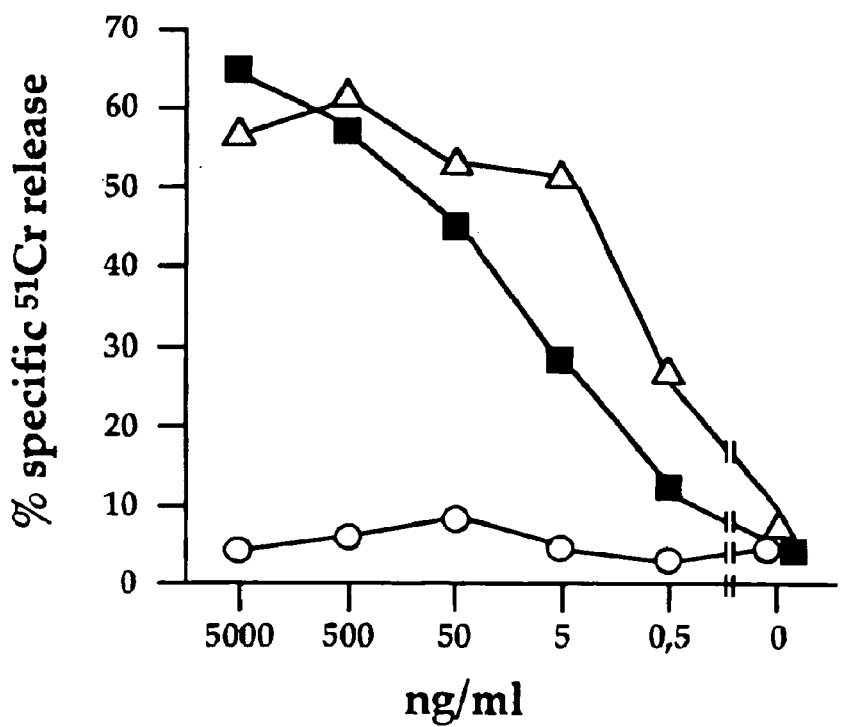

On FIG. 1B, the representative NK clone 3M16 was analyzed (% specific $^{51}$Cr release) in a redirected killing assay against P815 target cells (E/T ratio;1:1) in the presence of graded amounts of AZ20 (black squares), c127 (anti-CD16) (white triangles) or c128 (anti-CD56) (white circles) mAbs. All the mAbs used are of the IgG1 isotype.

Figure 1C:
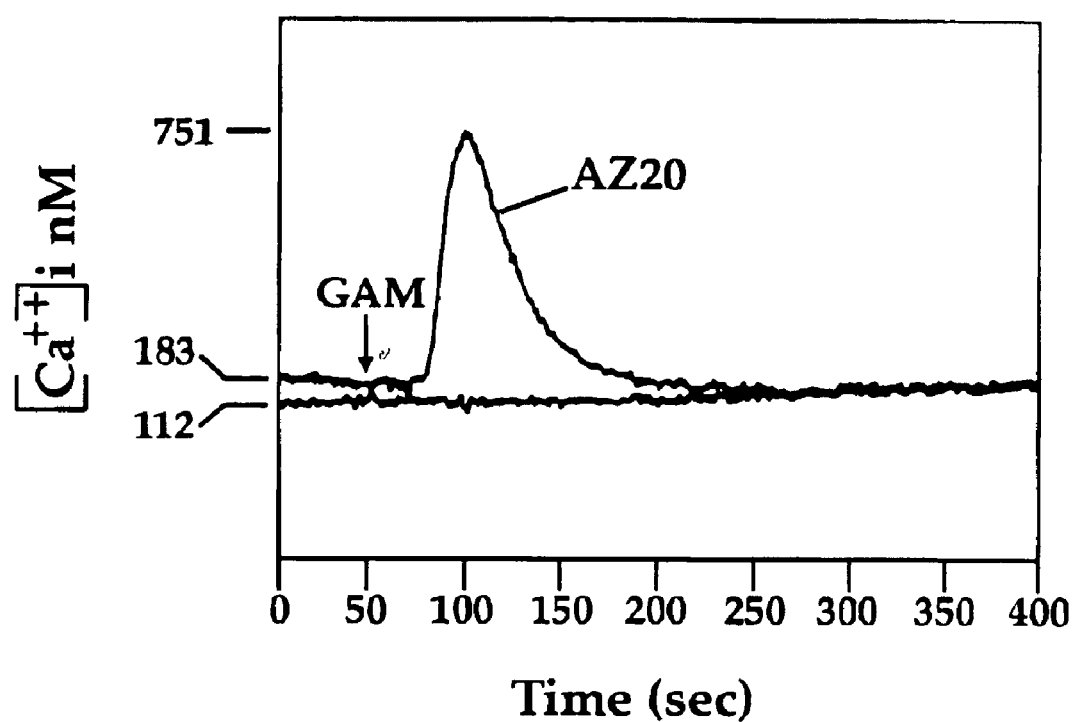

On FIG. 1C, clone 3M16 was analyzed for [Ca$^{++}$]i mobilization ([Ca$^{++}$]i nM as a function of time in seconds) in the presence of AZ20 mAb followed by goat anti-mouse second reagent (GAM). The negative control is represented by cells treated with GAM alone.

Figure 2A:
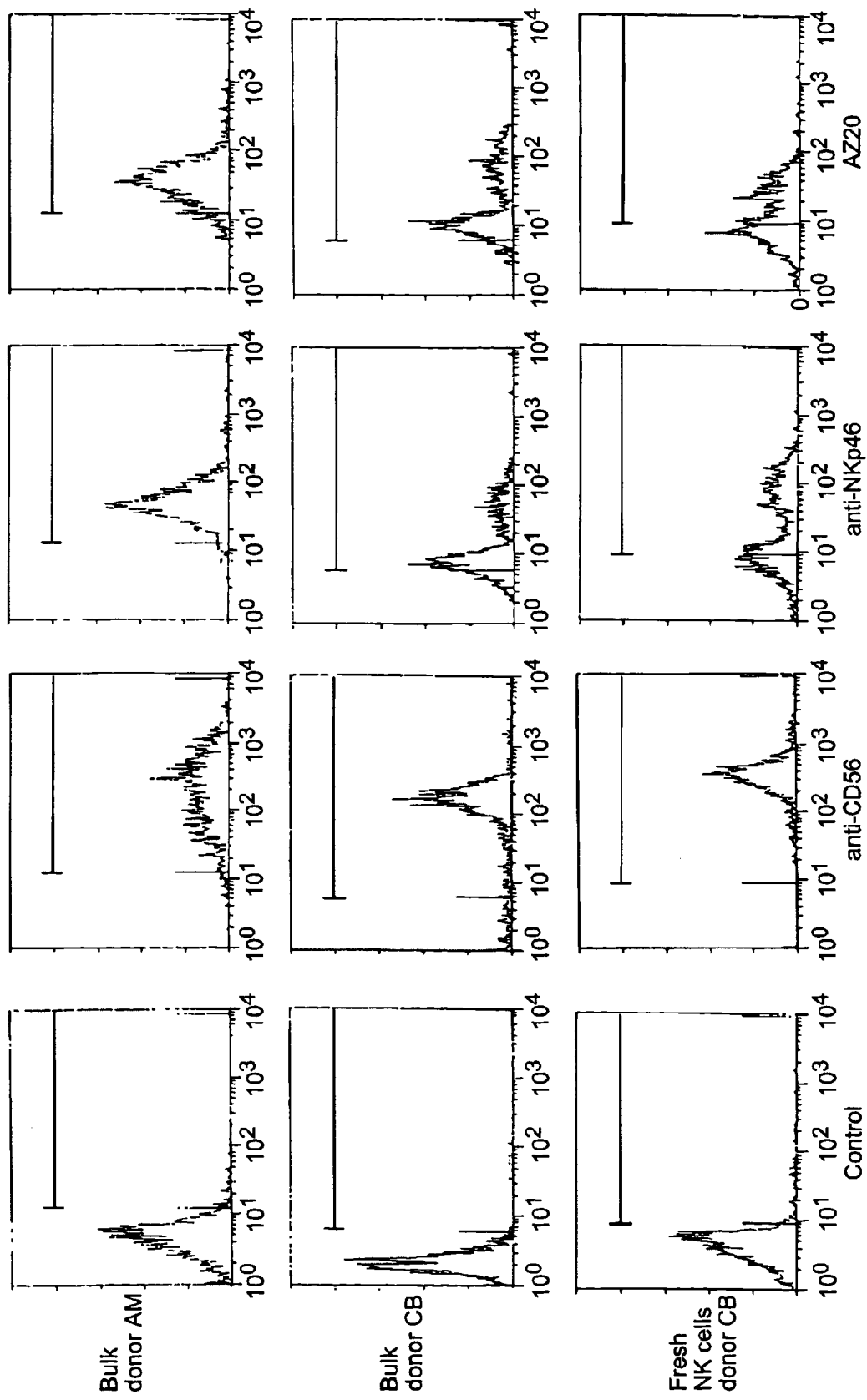
Figure 2B:
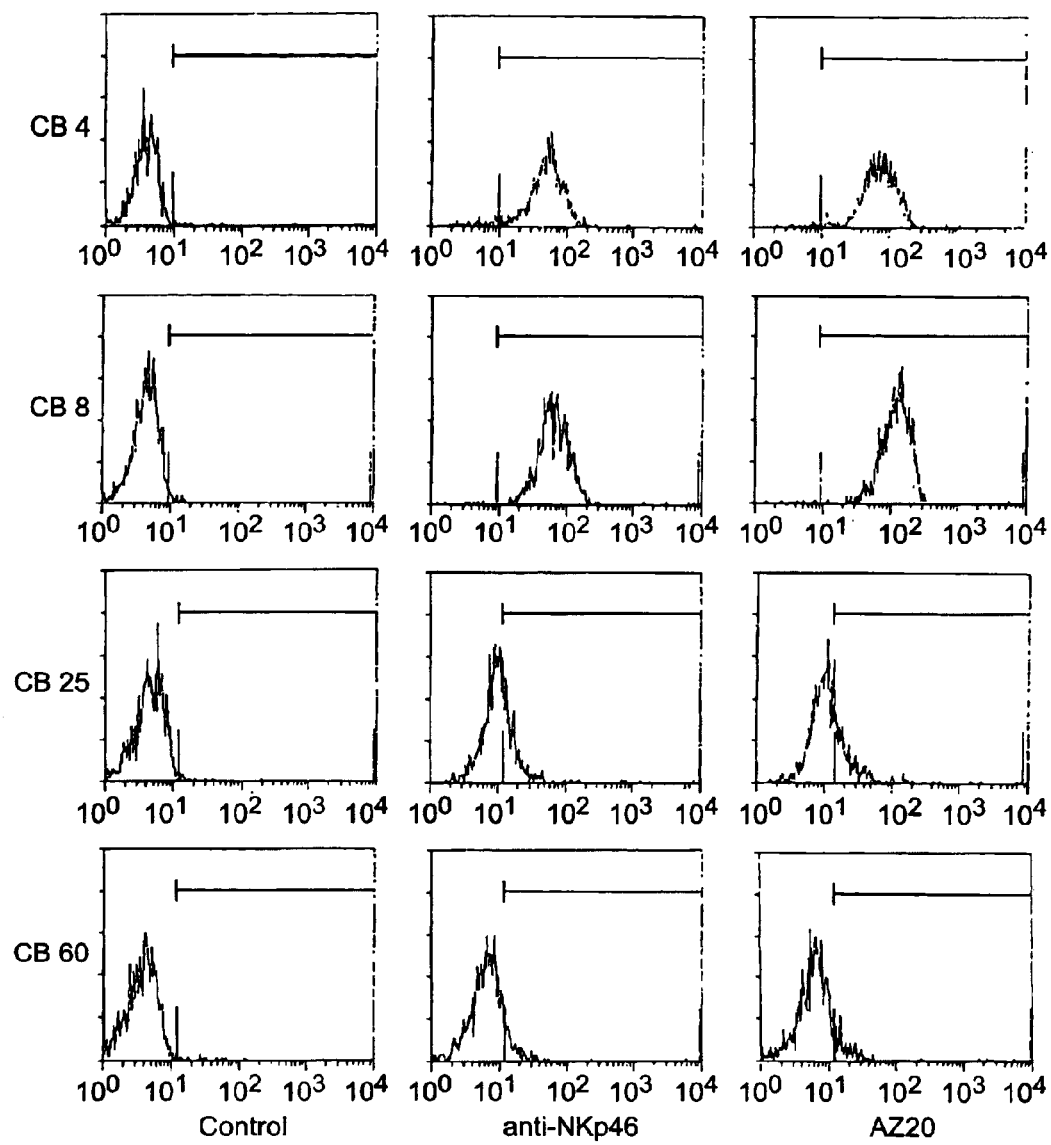

FIGS. 2A and 2B illustrates the cytofluorimetric analysis of resting or activated, polyclonal or clonal, NK cells.

On FIG. 2A, polyclonal NK cell populations, derived from donors AM and CB (upper and middle horizontal graph lines), and freshly isolated NK cells, derived from donor CB (lower horizontal graph lines), were analyzed by immunofluorescence and FACS analysis using c218 (anti-CD56; second vertical column), BAB281 (anti-NKp46); third vertical graph column) or AZ20 (anti-NKp30; last vertical graph column) mAbs followed by PE-conjugated goat anti-mouse IgG1. The control (first vertical graph column) is represented by cells incubated with the second reagent alone.

On FIG. 2B, NK cell clones, derived from donor CB, were analyzed by immunofluorescence and FACS analysis using BAB281 (anti-NKp46; vertical middle graph column) or AZ20 (anti-NKp30; vertical right-hand graph column) mAbs followed by PE-conjugated goat anti-mouse IgG1 (controls are represented on the vertical left-hand graph column).

Figure 3A:
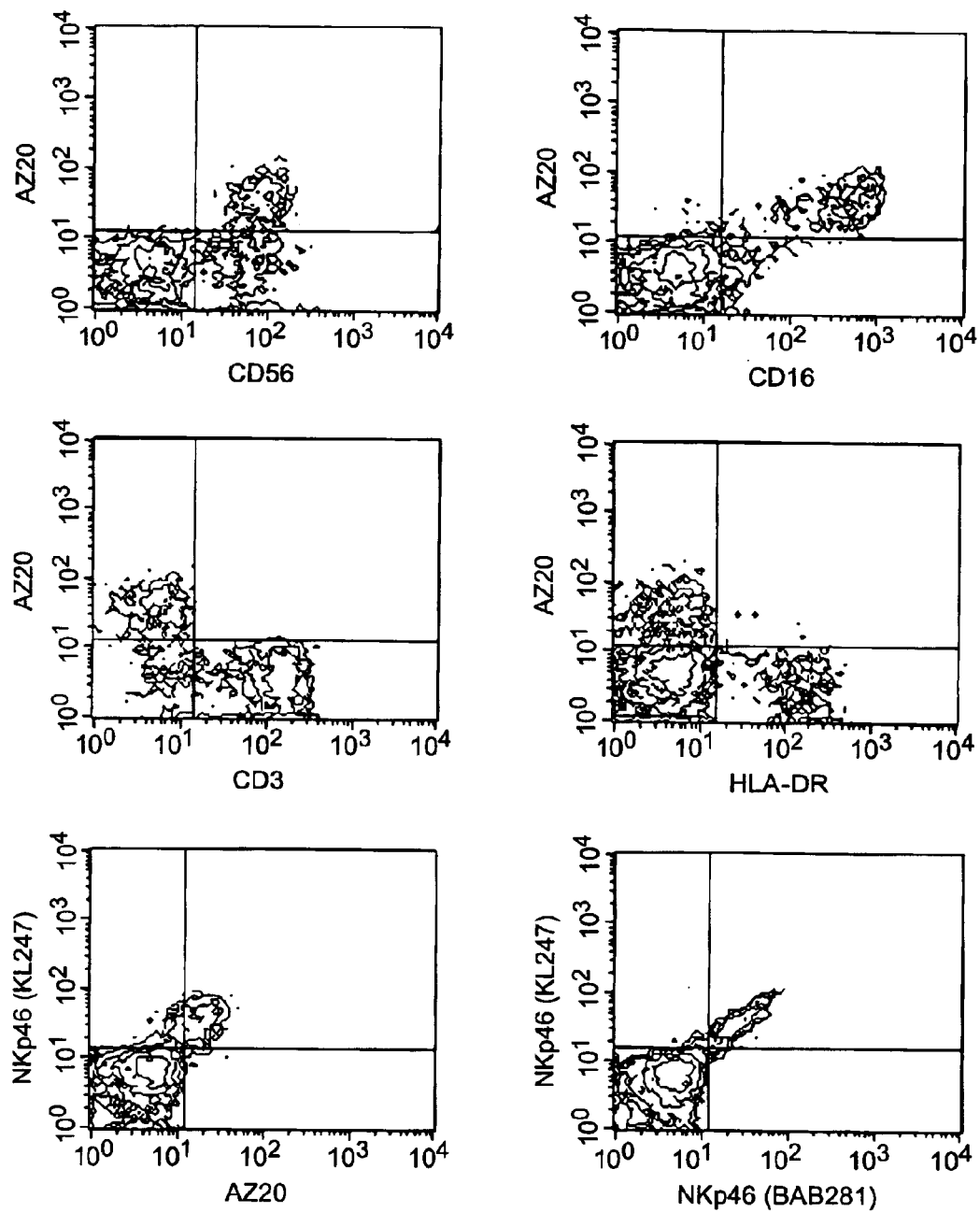
Figure 3B:
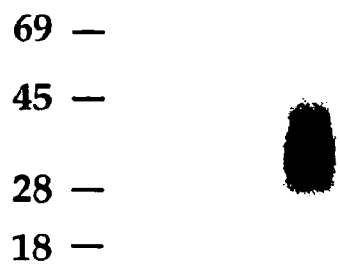

FIGS. 3A and 3B illustrate the pattern of expression of NKp30 in peripheral blood lymphocytes and Western blot analysis.

On FIG. 3A, freshly isolated peripheral blood lymphocytes, derived from a representative donor, were analyzed by two color immunofluorescence and FACS analysis with AZ20 mAb in combination with GPR 165 (IgG2a, anti-CD56), KD1 (lgG2a, anti-CD16), JT3A (IgG2a, anti-CD3), D1–12 (lG2a, anti-HLA-DR), KL247 (lgM, anti-NKp46) mAbs followed by isotype-specific FITC or PE-conjugated goat anti-mouse second reagents (upper left and right, middle left and right and lower left graphs). Double immunofluorescence with two anti-NKp46 mAbs of different isotype (KL247, lgM vs. BAB281, lgG1) is also shown (lower right). The contour plots were divided into quadrants representing unstained cells (lower left), cells with only red fluorescence (upper left), cells with red and green fluorescence (upper right) and cells with only green fluorescence (lower right).

On FIG. 3B, integral membrane proteins derived from Daudi (Burkitt lymphoma, negative control) and from a polyclonal NK cell population were analyzed in an 11% SDS-PAGE under non-reducing conditions and probed with AZ20 mAb. Molecular weight markers (kDa) are indicated on the left.

Figure 4A:
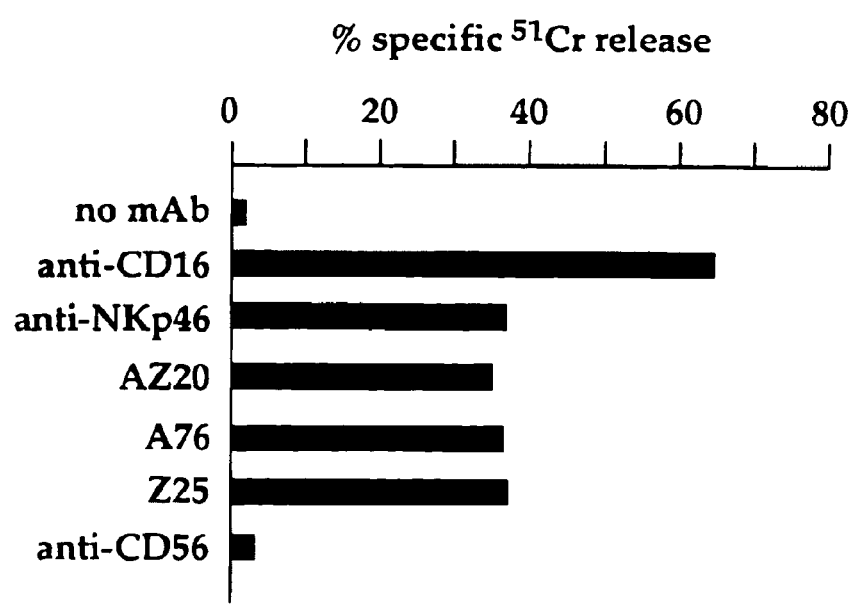
Figure 4B:
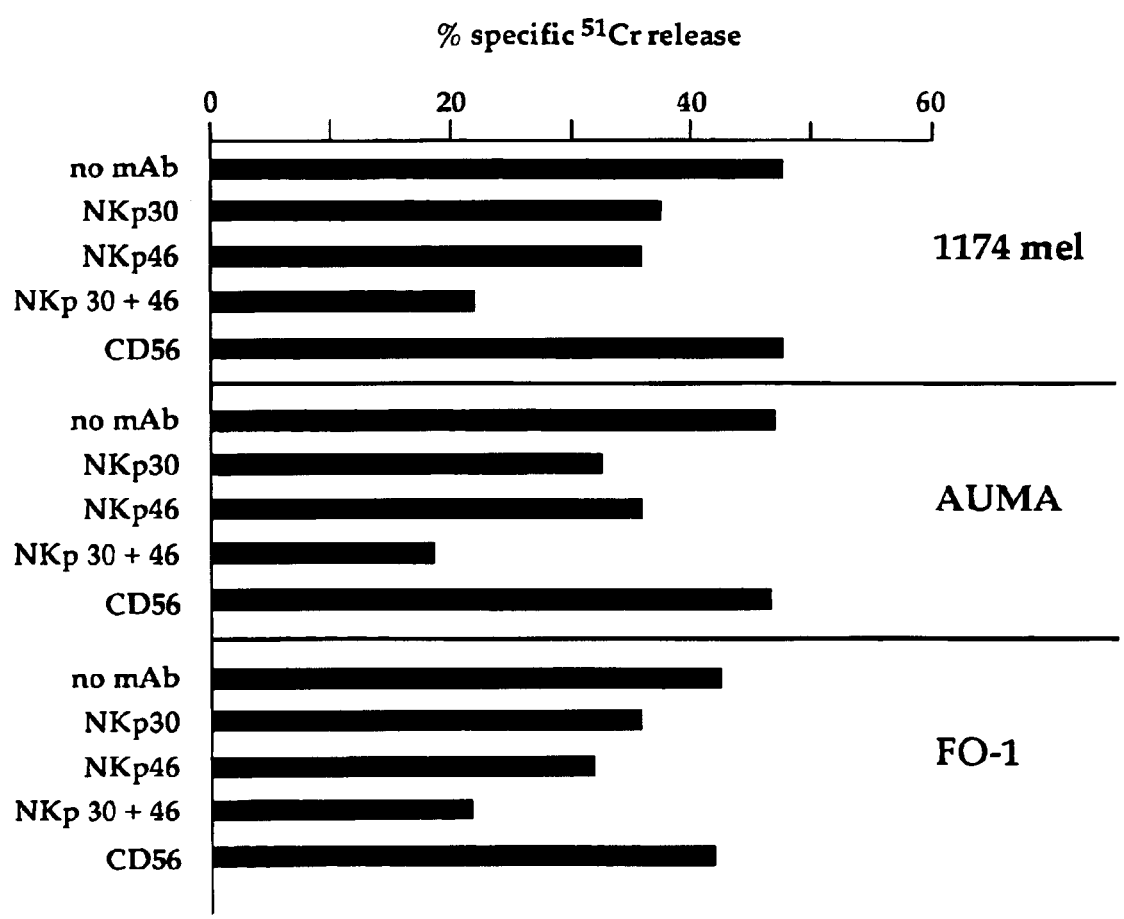

FIGS. 4A and 4B illustrate that NKp30 functions as an activating receptor in fresh NK cells and is involved in their natural cytotoxicity.

On FIG. 4A, freshly isolated peripheral blood NK lymphocytes, derived from a representative donor, were analyzed for cytolytic activity (% specific $^{51}$Cr release) in a redirected killing assay against the FcγR-positive P815 target cell line in the absence or in the presence of c127 (anti-CD16), BAB281 (anti-NKp46), AZ20, A76, Z25 and c218 (anti-CD56) mAbs. The E/T ratio used was 20:1.

On FIG. 4B, freshly isolated peripheral blood NK cells were analyzed for cytolytic activity against the indicated FcγR-negative/HLA class I-negative melanoma cell lines either in the absence or in the presence of mAbs to the indicated molecules: c218 (anti-CD56), AZ20 (anti-NKp30), BAB281 (anti-NKp46) mAbs were used. The E/T ratio was 20:1.

Figure 5:
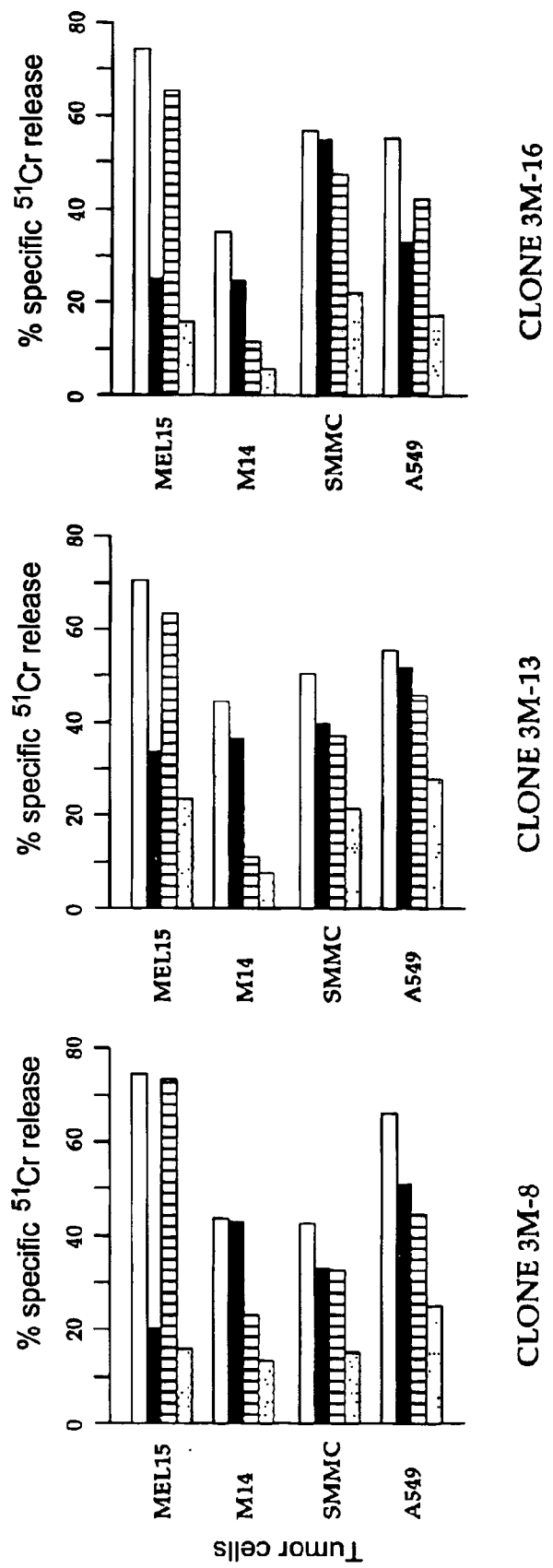

FIG. 5 illustrates the involvement of NKp30 and NKp46 in the tumor cell lysis mediated by NK cell clones. Three NK cell clones were analyzed for cytolytic activity against MEL 15, M14, SMMC and A549 FcγR-negative target cell lines either in the absence (white bars) or in the presence of AZ20 (anti-NKp30; black bars), BAB281 (anti-NKp46; striped bars) or both AZ20 and BAB281 (stippled bars) mAbs. The E/T ratio was 4:1.

Figure 6A:
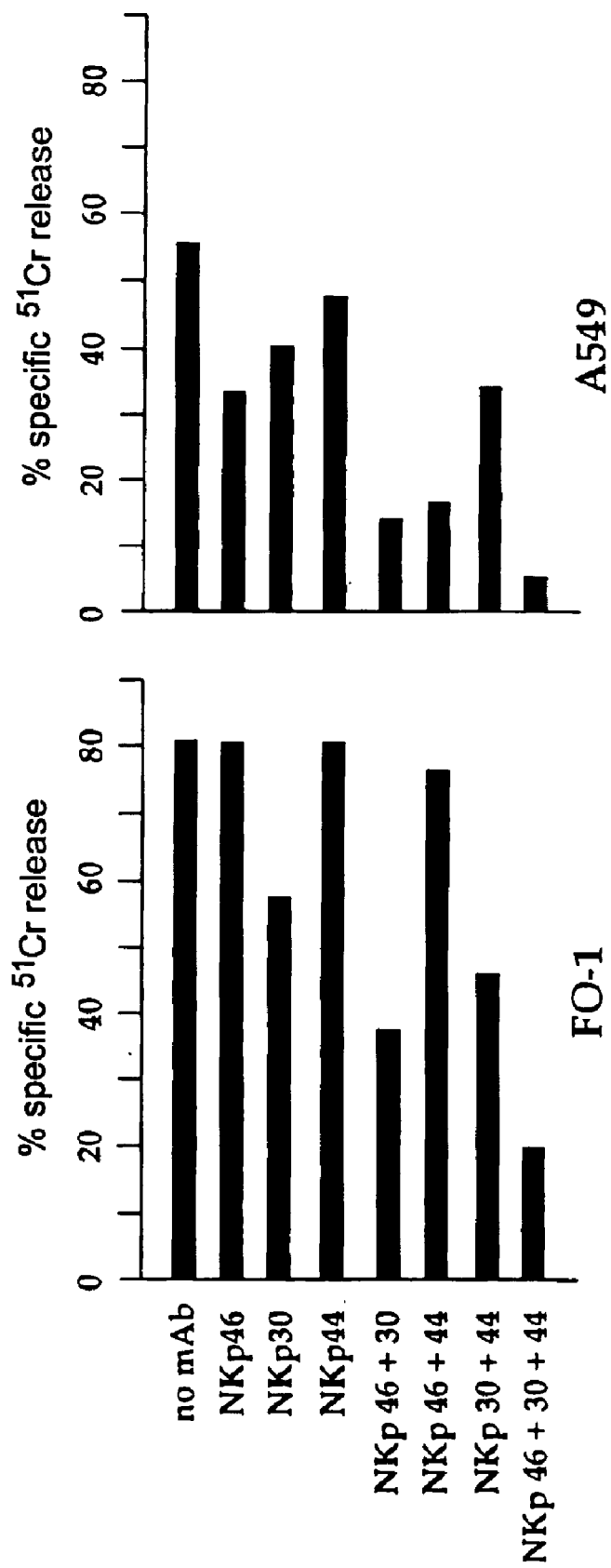

FIGS. 6A and 6B illustrate that NKp30 co-operates with NKp46 and NKp44 in the induction of NK-mediated cytotoxicity against tumor or normal autologous target cells.

On FIG. 6A, the representative NK clone MIL69 was analyzed for cytolytic activity (% specific $^{51}$Cr release) against FO-1 or A549 FcγR-negative target cell lines either in the absence or in the presence of mAbs to the indicated molecules. The following mAbs were used: KL247 (anti-NKp46), AZ20 (anti-NKp30), KS38 (anti-NKp44). The E/T ratios were 2:1 (FO-1) and 3:1 (A549).

On FIG. 6B, two NK cell clones (MX361 and P9) were analyzed (% specific $^{51}$Cr release) for cytolytic activity against autologous PHA Blasts either in the absence (white bars) or in the presence of mAbs to the indicated molecules (black bars). The mAbs used were A6-136 (anti-HLA class I), KL247 (anti-NKp46), KS38 (anti-NKp44), AZ20 (anti-NKp30). The E/T ratio as 10:1.

Figure 7A:
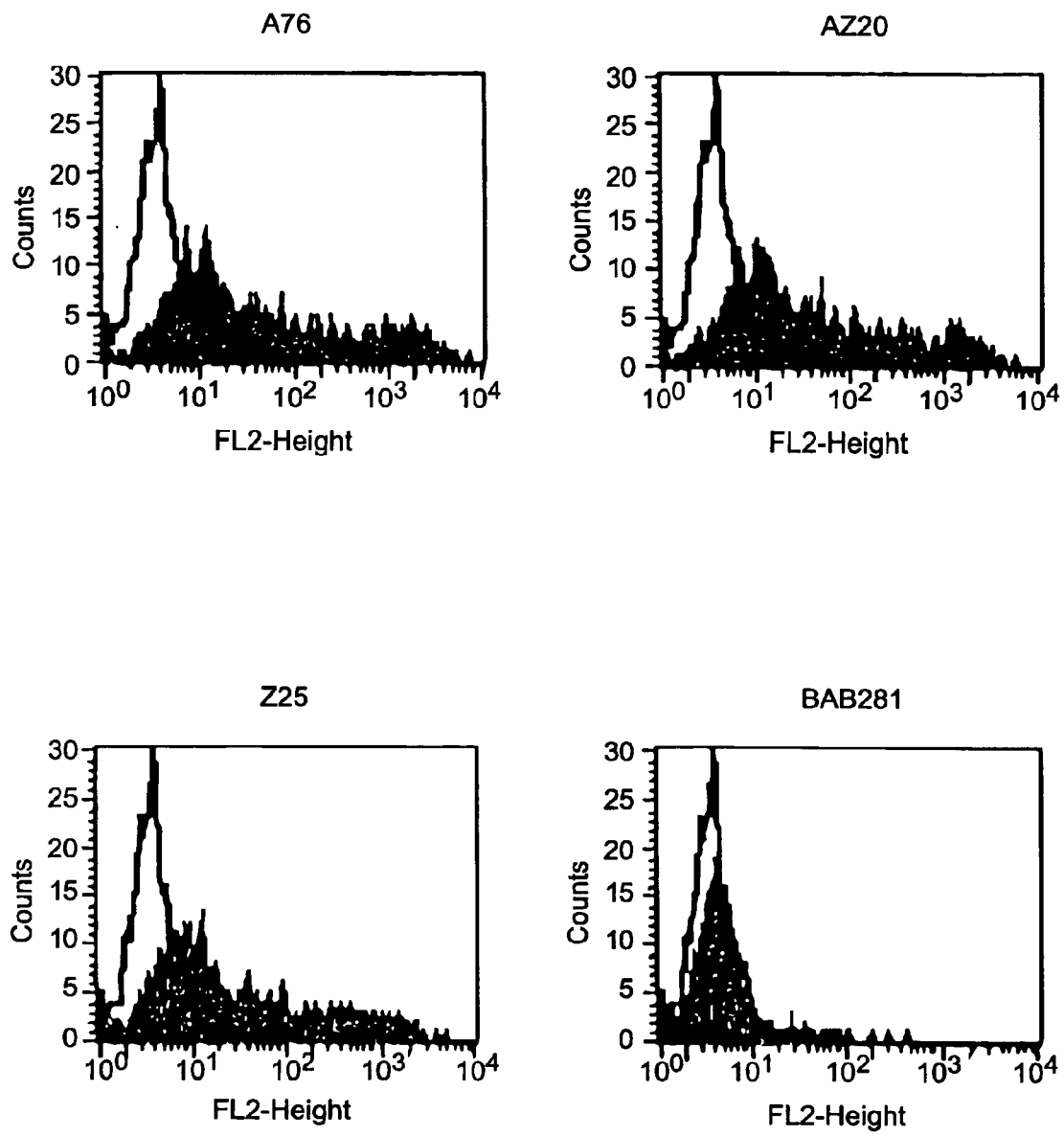
Figure 7B:
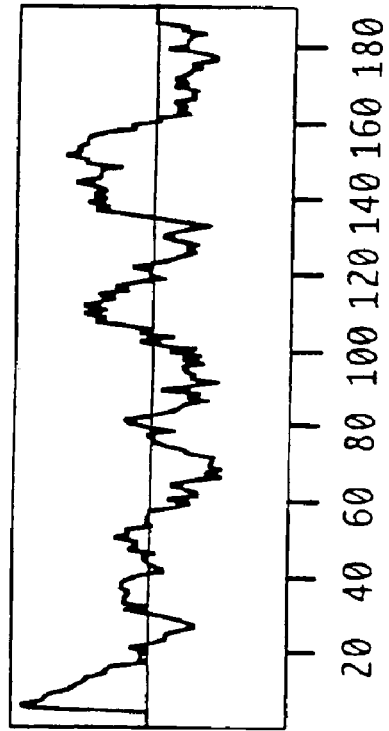

FIGS. 7A, 7B and 7C illustrate the cytofluorimetric analysis of the NKp30 molecules expressed in COS-7 cell transfectants; amino acid sequence (SEQ ID NO: 2) and hydrophobicity plot of NKp30.

On FIG. 7A, COS-7 cells, transfected with clone 5C cDNA construct were stained with anti-NKp30 (from left to right: A76, AZ20, Z25) or with anti-NKp46 (BAB 281) mAbs followed by PE-conjugated goat anti-mouse lgG1 and analyzed by flow cytometry. White profiles represent cells incubated with the second reagent alone (i.e. negative controls).

On FIG. 7B (illustrating SEQ ID NO: 2), the signal peptide (SEQ ID NO: 3) is indicated in lower case letters, the transmembrane region (SEQ ID NO: 5) is underlined. The NKp30 extracellular region sequence (SEQ ID NO: 4) corresponds to the sequence given between the signal peptide and the transmembrane region. The NKp30 intracellular region sequence (SEQ ID NO: 6) corresponds to the sequence given after (C-terminal) the transmembrane sequence. Cysteines involved in the lg-like fold are circled, putative N-glycosylation sites are boxed. Kyte-Doolittle hydrophobicity plot is shown on the bottom. DNA and protein sequence analysis were performed using GeneWorks, MacVector suites, NetOGlyc 2.0 (worldwide web site cbs.dtu.dk/services/NetOGlyc) and PSORT Prediction Servers (worldwide web site psort.nibb.ac.jp:8800/). On FIG. 7C, is represented the NKp30 cDNA sequence (SEQ ID NO: 1) NKp30 coding sequence is from position 64 to position 636 (SEQ ID NO: 13). The 421 bp cDNA probe (SEQ ID NO: 10) for NKp30 corresponds to the sequence given from position 57 to position 477 of DEQ ID NO: 1. The 606 bp cDNA (SEQ ID NO: 12) amplified from NKp30 for cloning in pCR2.1 corresponds to the sequence given from position 57 to position 662 of SEQ ID NO: 1.

Figure 8A:
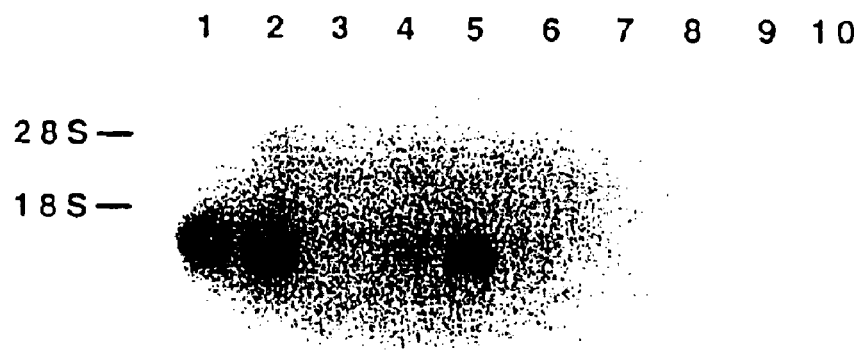
Figure 8B:
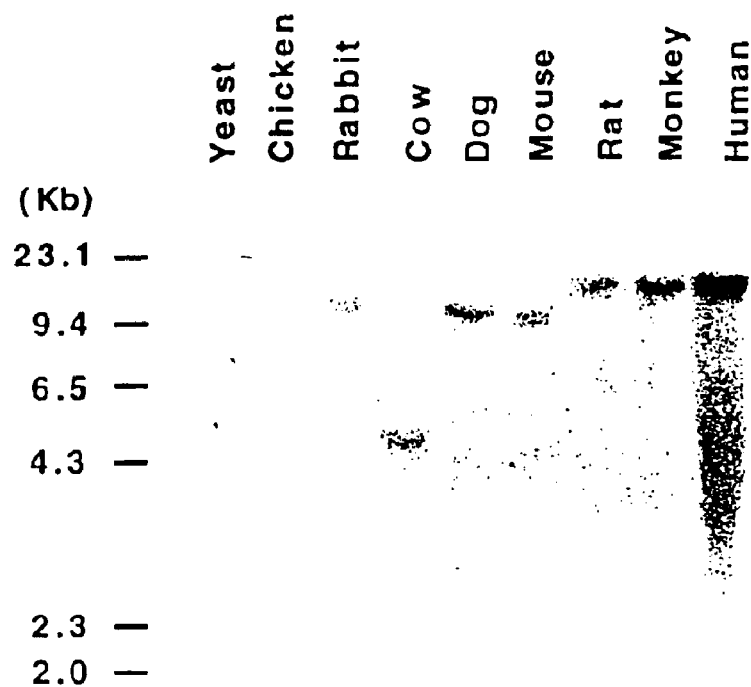

FIGS. 8A and 8B illustrate the Northern blot analysis of NKp30 transcript expression and Zoo-blot analysis.

On FIG. 8A, total RNA was isolated from cells of different origin. Lanes 1 and 2: polyclonal NK cell populations; lane 3: blank; lane 4: a NK cell line (NKL); lane 5: a NK cell line (NK3.3); lane 6: human monocytes; lane 7: a histiocytic lymphoma cell line (U937); lane 8: a T lymphoma cell line (Jurkat); lane 9: an acute promyelocytic leukemia cell line (HL60); lane 10: an EBV-transformed B cell line (LCL721.221). Ten microgrammes of each RNA preparation (2 microgrammes of poly A+ RNA from polyclonal NK cell populations (lanes 1 and 2)) were hybridized with the 421 bp NKp30 cDNA probe. The positions of 28S and 18S ribosomal RNA subunits are indicated on the left.

On FIG. 8B, a Southern blot containing genomic DNA from Human, Rhesus monkey, Sprague-Dawley rat, BALB/c mouse, dog, cow, rabbit, chicken and *Saccharomyces cerevisiae* yeast was hybridized under low stringency condition with the 421 bp NKp30 cDNA probe.

Figure 9A:
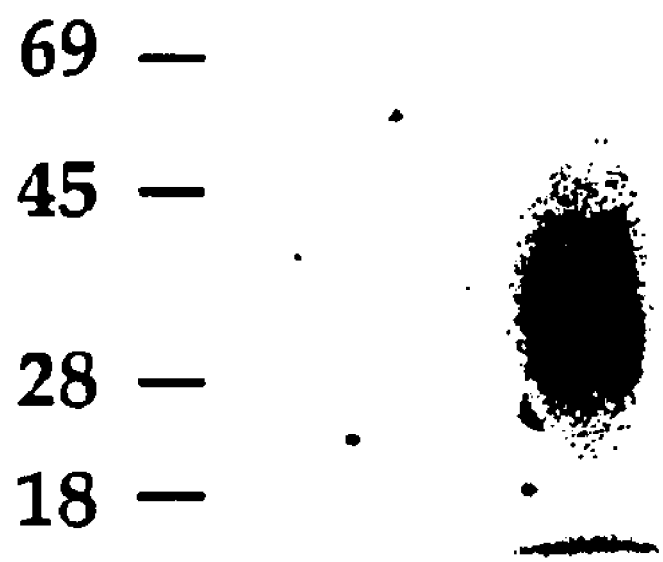
Figure 9B:
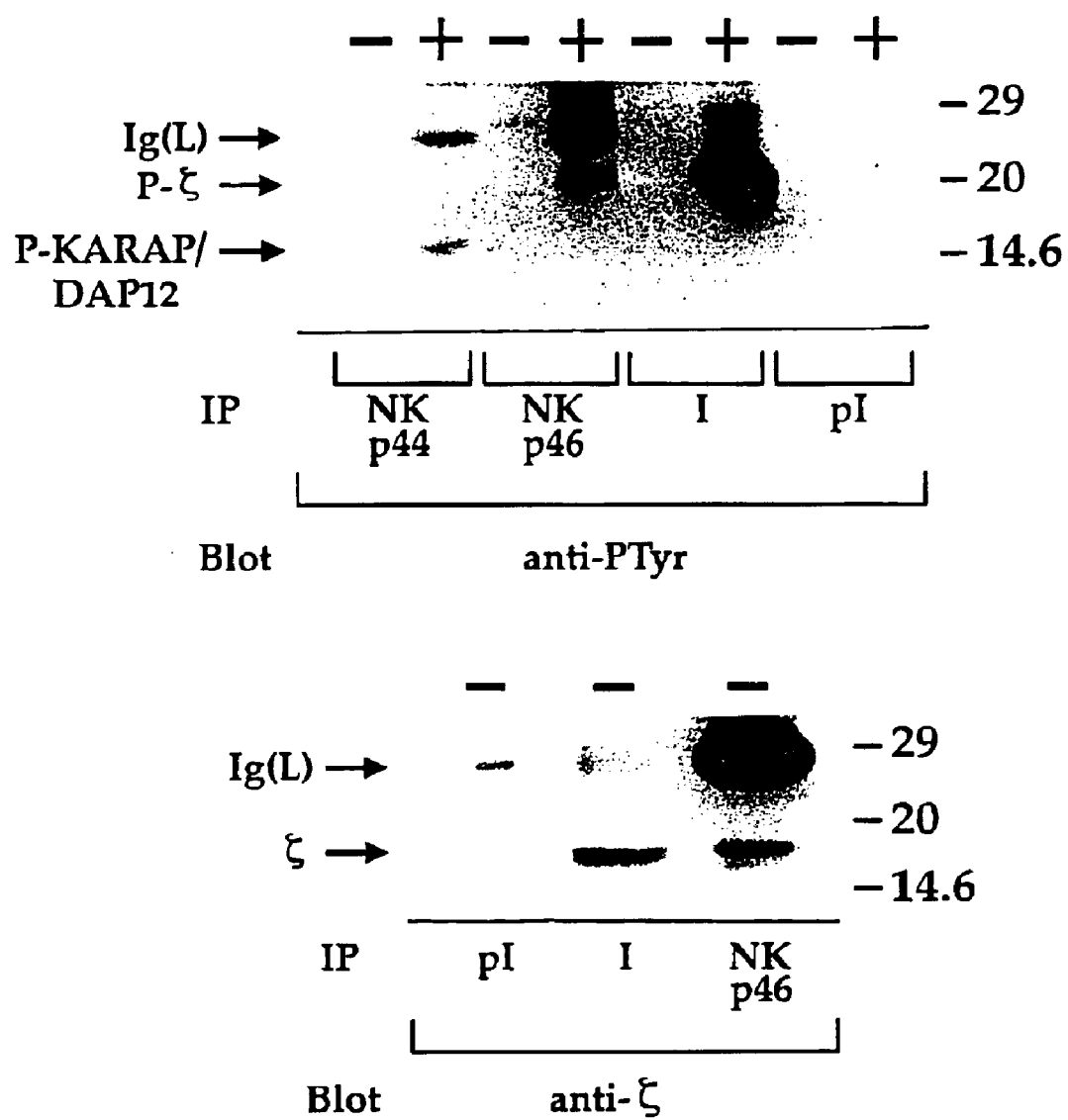

FIGS. 9A and 9B illustrate the biochemical analysis of the NKp30 receptor complex by the use of a specific antiserum.

On FIG. 9A, integral membrane proteins derived from Daudi (as negative control) and from a polyclonal NK cell population were analyzed in an 11% SDS-PAGE under non-reducing conditions and probed with NKp30-specific rabbit antiserum (I). Molecular weight markers (kDa) are indicated on the left.

On FIG. 9B, 1% Digitonin cell lysates derived from a polyclonal NK cell population untreated (−) or treated (+) with sodium pervanadate, were immunoprecipitated with Z231 mAb (anti-NKp44), BAB281 mAb (anti-NKp46), NKp30-specific rabbit antiserum (l) and pre-immune rabbit serum (pI), Samples were analyzed in a 15% SDS-PAGE under reducing conditions and probed with either anti-phosphotyrosine (anti-PTyr) or anti-CD3ζ (anti-ζ) mAbs. lg light chains (lg(L)), Tyr-phosphorylated CD3ζ (P-ζ), Tyr-phosphorylated KARAP/DAP12 (P-KARAP/DAP12) and the non phosphorylated form of CD3ζ are indicated by arrows. Molecular weight markers (in kDa) are indicated on the right.

EXAMPLE 1

Identification and Molecular Characterization of NKp30

MATERIAL AND METHODS

Monoclonal antibodies (mAbs)

The following mAbs were produced in our lab: JT3A (lgG2a, anti-CD3), BAB281 (Sivori, S., M. Vitale, L. Morelli, L. Sanseverino, R. Augugliaro, C. Bottino, L. Moretta, and A. Moretta. 1997. p46, a novel Natural Killer cell-specific surface molecule which mediates cell activation. *J. Exp. Med.* 186:1129–1136) and KL247 (lgG1 and lgM, respectively, anti-NKp46), Z231 (Vitale; M., C. Bottino, S. Sivori, L. Sanseverino, R. Castriconi, R. Marcenaro, R. Augugliaro, L. Moretta, and A. Moretta. 1998. NKp44, a novel triggering surface molecule specifically expressed by activated Natural Killer cells is involved in non-MHC restricted tumor cell lysis. *J. Exp. Med.* 187:2065–2072) and KS38 (lgG1 and lgM, respectively, anti-NKp44), KD1 and c127 (lgG2a and lgG1, respectively, anti-CD16), c218 and GPR165 (lgG1 and lgG2a, respectively, anti-CD56), A6-136 (lgM, anti-HLA class I) (Ciccone E., D. Pende, M. Vitale, L. Nanni, C. Di Donato, C. Bottino, L. Morelli, O. Viale, A. Amoroso, A. Moretta, and L. Moretta. 1994. Self Class I molecules protect normal cells from lysis mediated by autologous Natural Killer Cells. *Eur. J. Immunol.* 24:1003–1006), GL183 (lgG1, anti-p58.2) (Moretta A., G. Tambussi, C. Bottino, G. Tripodi, A. Merli, E. Ciccone, G. Pantaleo, and L. Moretta. 1990. A novel surface antigen expressed by a subset of human CD3–CD16+ Natural Killer cells. Role in cell activation and regulation of cytolytic function. *J. Exp. Med.* 171:695–714), EB6 (lgG1, anti-p58.1) (Moretta A., C. Bottino, D. Pende, G. Tripodi, G. Tambussi, O. Viale, A. M. Orengo, M. Barbaresi, A. Merli, E. Ciccone, and L. Moretta. 1990. Identification of four subsets of human CD3–CD16+ NK cells by the expression of clonally distributed functional surface molecules. Correlation between subset assignment of NK clones and ability to mediate specific alloantigen recognition. *J. Exp. Med.* 172:1589–1598), Z199 (lgG2b, anti-NKG2A) (Sivori, S., M. Vitale, C. Bottino, E. Marcenaro, L. Sanseverino, S. Parolini, L. Moretta, and A. Moretta, 1996. CD94 functions as a natural killer cell inhibitory receptor for different HLA-CLASS-I alleles. Identification of the inhibitory form of CD94 by the use of novel monoclonal antibodies. *Eur. J. Immunol.* 26:2487–2492). D1.12 (lgG2a) mAb and HP2.6 (lgG2a) mAb were used as anti-HLA-DR, and anti-CD4, respectively.

The novel mAbs were first conventionally derived by immunizing 5-wk-old Balb/C mice with activated (CD3−, CD56+, CD16+) NK cells either NK clones (EC1 and SA260, for A76 and Z25 mAbs respectively) or a polyclonal NK cell population (for AZ20 mAb). After different cell fusions, the mAbs were selected for the ability to induce lysis in redirected killing assays against the FcγR+ P815 target cells. Appropriate mAbs include those which induce a statistically significant (p<0.05) increase in NK cell activation as assessed by (i) natural cytotoxicity towards MHC class I negative targets, tumor cells, virally-infected cells, allogeneic cells, (ii) cytotoxicity towards antibody-coated target cells, (iii) increases in intracytoplasmic Ca2+ concentration, (iv) induction of tyrosine phosphorylation of intracytoplasmic adaptor/effector molecules such a ZAP70, Syk, LAT, SLP76, Shc, Grb2, phospholipase C-gamma enzymes, phosphatidyl-inositol 3 -kinases, (vi) phosphorylation of receptor-associated transducing chains KARAP/DAP12 or CD3zeta or FcRgamma, (vi) cytokine secretion such as interferon gamma, tumor necrosis factors, IL5, IL10, chemokines (such as MIP-lalpha), TGFbeta, (vii) up- or down-regulation of NK cell surface molecules, such as CD69 and PEN5 respectively. Preferred mAbs induce e.g. an induce an increase of at least about 5 in target cell lysis with an effector:target (E:T) ratio of 1:1 when compared to the basic target cell lysis performed by the effector NK cells in the absence of said mAbs. Three mAbs were thus selected: A76; Z25; and AZ20.

Purification of Peripheral Blood Lymphocytes (PBL) and Generation of Polyclonal or Clonal NK Cell Populations Peripheral blood lymphocytes (PBL) were derived from healthy donors by Ficoll-Hipaque gradients and depletion of plastic-adherent cells. In order to obtain enriched NK cells PBL were incubated with anti-CD3 (JT3A), anti-CD4 (HP2.6) and anti-HLA-DR (D1.12) mAbs (30 min at 4° C.) followed by goat anti-mouse coated Dynabeads (Dynal, Oslo, Norway) (30 min at 4° C.) and immunomagnetic depletion (Pende, D., L. Accame, L. Pareti, A. Mazzocchi, A. Moretta, G. Parmiani, and L. Moretta. 1998. The susceptibility to Natural Killer cell-mediated lysis of HLA class I-positive melanomas reflects the expression of insufficient amounts of HLA class I alleles. Eur. J. Immunol. 28:2384–2394 ; Sivori, S., M. Vitale, L. Morelli, L. Sanseverino, R. Augugliaro, C. Bottino, L. Moretta, and A. Moretta. 1997. p46, a novel Natural Killer cell-specific surface molecule which mediates cell activation. J. Exp. Med. 186:1129–1136 ; Vitale, M., C. Bottino, S. Sivori, L. Sanseverino, R. Castriconi, R. Marcenaro, R. Augugliaro, L. Moretta, and A. Moretta. 1998. NKp44, a novel triggering surface molecule specifically expressed by activated Natural Killer cells is involved in non-MHC restricted tumor cell lysis. J. Exp. Med. 187:2065–2072). CD3⁻4⁻DR⁻ cells were used in cytolytic assays or cultured on irradiated feeder cells in the presence of 100 U/ml rIL-2 (Proleukin, Chiron Corp., Emeryville, USA) and 1.5 ng/ml PHA (Gibco Ltd, Paisley, Scotland) in order to obtain polyclonal NK cell populations or, after limiting dilution), NK cell clones (Moretta, A. 1985. Frequency and surface phenotype of human T lymphocytes producing interleukin-2. Analysis by limiting dilution and cell cloning. Eur. J. Immunol. 151:148–155).

Flow Cytofluorimetric Analysis

Cells were stained with the appropriate mAb followed by PE- or FITC-conjugated isotype-specific goat anti-mouse second regent (Southern Biotechnology Associated, Birmingham, Ala.). Samples were analyzed by one-or two-color cytofluorimetric analysis (FACScan Becton Dickinson & Co, Mountain View, Calif.) as previously described (e.g. Moretta A., G. Tambussi, C. Bottino, G. Tripodi, A. Merli, E. Ciccone, G. Pantaleo, and L. Moretta. 1990. A novel surface antigen expressed by a subset of human CD3–CD16+ Natural Killer cells. Role in cell activation and regulation of cytolytic function. J. Exp. Med. 171:695–714).

Cell Lines and Cytolytic Assays

The FcγR-negative targets used were the following: MEL15 (MEL15392, human melanoma) (Pende, D., L. Accame, L. Pareti, A. Mazzocchi, A. Moretta, G. Parmiani, and L. Moretta. 1998. The susceptibility to Natural Killer cell-mediated lysis of HLA class I-positive melanomas reflects the expression of insufficient amounts of HLA class I alleles. Eur. J. Immunol. 28:2384–2394); M14 (human melanoma) (Pessino, A., S. Sivori, C. Bottino, A. Malaspina, L. Morelli, L. Moretta, R. Biassoni, and A. Moretta. 1998. Molecular cloning of NKp46: a novel member of the immunoglobulin superfamily involved in triggering of natural cytotoxicity. J. Exp. Med. 188:953–960) ; SMMC (human hepatocarcinoma) (Sivori, S., D. Pende, C. Bottino, E. Marcenaro, A. Pessino, R. Biassoni, L. Moretta, and A. Moretta. 1999. NKp46 is the major triggering receptor involved in the natural cytotoxicity of fresh or cultured human natural killer cells. Correlation between surface density of NKp46 and natural cytotoxicity against autologous, allogeneic or xenogeneic target cells. Eur. J. Immunol. 29:1656–1666); A549 (human lung adenocarcinoma; ATCC number CCL-185.1); FO-1 and 1174 mel (human melanomas); AUMA (human melanoma).

The FcγR-positive target used was P815 (murine mastocytoma). PHA-Blasts, used as normal target cells, were obtained by culturing PBL with 1.5 ng/ml PHA (Gibco).

Cells were tested for cytolytic activity in a 4-h $^{51}$Cr-release assay as previously described), either in the absence or in the presence of various mAbs (Moretta A., C. Bottino, D. Pende, G. Tripodi, G. Tambussi, O. Viale, A. M. Orengo, M. Barbaresi, A. Merli, E. Ciccone, and L. Moretta. 1990. Identification of four subset of human CD3–CD16+ NK cells by the expression of clonally distributed functional surface molecules. Correlation between subset assignment of NK clones and ability to mediate specific alloantigen recognition. J. Exp. Med. 172:1589–1598-; Sivori, S., D. Pende, C. Bottino, E. Marcenaro, A. Pessino, R. Biassoni, L. Morefta, and A. Moretta. 1999. NKp46 is the major triggering receptor involved in the natural cytotoxicity of fresh or cultured human natural killer cells. Correlation between surface density of NKp46 and natural cytotoxicity against autologous, allogeneic or xenogeneic target cells. Eur. J. Immunol. 29:1656–1666). The concentrations of the various mAbs were 10 microgrammes/ml for the masking experiments and 0.5 microgrammes/ml for the redirected killing experiments. The E/T ratios are indicated in the text. Appropriate mAbs include those which significantly increase the cytolytic activity observed in their absence. Examples of such an appropriate significant increase comprise an increase of at least about 5 times of the cytolytic activity observed with an effector: target ratio of 1:1 in the presence of said mAbs when compared to the cytolytic activity observed in the absence of these mAbs.

Determination of Intracellular Free Calcium [Ca++]i Increase

Determination of [Ca++]i was performed as previously described (Poggi A., R. Pardi, N. Pella, L. Morelli, S. Sivori, M. Vitale, V. Revello, A. Moretta, and L. Moretta. 1993-CD45-mediated regulation of LFA1 function in human natural killer cells. Anti-CD45 monclonal antibodies inhibit the calcium mobilization induced via LFA1 molecules. Eur. J. Immunol. 23:2445–2463). Fura-2-labeled NK cells were incubated for 30' at 4° C. with saturating amounts of anti-NKp30 mAb (AZ20) or medium alone. Cross-linking of this receptor was obtained by adding into the cuvefte 20 μg/ml of affinity purified Goat Anti-Mouse antiserum (GAM) (ICN Biomedicals, Aurora, Ohio).

Biochemical Characterization of the NKp30 Molecules

Integral NK cell membrane proteins (Bordier, C. 1981. Phase separation of integral membrane proteins in Triton X-114 solution. J. Biol. Chem. 256:1604–1606) were prepared as follows: 25×10⁶ cells were lysed in 100 μl TX buffer (20 mM Sodium phosphate buffer, 1% Triton X-114, 10 mM EDTA, pH 8) 30' at 4° C., centrifuged (5', 10.000 RPM). The supernatant was left 10'at 37° C., centrifuged and lower phase was resuspended 1:2 in TX buffer and left 10' at 4° C. in order to clarify the lysates. The suspension was then left 10' at 37° C, centrifuged and the lower phase resuspended 1:3 in EB (0.0625 M Tris pH6.8, 10% Glycerol, 2.3% SDS). Samples were analyzed in discontinuous SDS-PAGE, transferred to Immobilon P (Millipore Corp, Bedford, Mass.) and probed with AZ20 mAb followed by rabbit anti-mouse HRPO (DAKO A/S, Denmark) or NKp30-specific antiserum followed by donkey anti-rabbit HRPO (Amersham, Buckingamshire, UK). The Renaissance Chemiluminescence Kit (NEN, Boston, Mass.) was used for detection.

NKp30 Polyclonal Antiserum

A 2.5 kg HY/Cr male rabbit (Charles River) was immunized with 100 microgrammes/100 microliters of the 15aa peptide WVSQPPEIRTLEGSC (SEQ ID NO: 7 from amino acid position 20 to position 33 in NKp30 protein sequence SEQ ID NO: 2, plus a C amino acid for linkage to KLH) conjugated with KLH (Pende D., R. Biassoni, C. Cantoni,. S. Verdiani, M. Falco, C. Di Donato, L. Accame, C. Bottino, A. Moretta, and L. Moretta. 1996. The Natural Killer cell receptor specific for HLA.A allotypes: a novel member of the p58/p70 family of inhibitory receptors that is characterized. by three immunoglobulin-like domains and is expressed as a 140 kD disulphide-linked dimer. J. Exp. Med. 184:505–518). Four weekly treatments were performed, the first in association with 100 microliters complete Freund adjuvant all the other with 100 microliters incomplete Freund adjuvant. After one week from the last treatment 10 ml of blood was drought and serum was tested and titred by ELISA against the immunizing peptide and irrelevant ones.

Analysis of the NKp30 Signal Transduction Complex

NK cells ($10^8$) were stimulated or not with 100 microM sodium pervanadate (Cantoni, C., C. Bottino, M. Vitale, A. Pessino, R. Augugliaro, A. Malaspina, S. Parolini, L. Moretta, A. Moretta, and R. Biassoni. 1999. NKp44, a triggering receptor involved in tumor cell lysis by activated human Natural Killer cells, is a novel member of the immunoglobulin superfamily. J. Exp. Med. 189:787–796) and 1% Digitonin lysates were precleared five times with Sepharose Protein A-coupled KDI (anti-CD16) mAb. Lysates were then immunoprecipitated with Sepharose-CNBr-coupled Z231 and BAB281 mAbs or with Sepharose Protein A-coupled NKp30-specific rabbit antiserum and pre-immune rabbit serum. Samples were analyzed in a 15% SDS-PAGE under reducing conditions (5% 2Me), transferred to Immobilon P (Millipore) and probed with anti-phosphotyrosine mAb (PY20-HRPO, Transduction Laboratories, Lexington, KY) or anti-CD3ζ mAb (2H2, Immunotech, Marseille, France) followed by rabbit anti-mouse HRPO (DAKO). The Renaissance Chemiluminescence Kit (NEN) was used for detection.

Library Screening by cDNA Expression in COS-7 Cells

The expression cDNA library was prepared in VR1012 plasmid (Vical Inc., San Diego, Calif.), using RNA extracted from IL-2-activated polyclonal NK cells obtained from two healthy donors as previously described (Pessino, A., S. Sivori, C. Bottino, A. Malaspina, L. Morelli, L. Moretta, R. Biassoni, and A. Moretta. 1998. Molecular cloning of NKp46: a novel member of the immunoglobulin superfamily involved in triggering of natural cytotoxicity. J. Exp. Med. 188:953–960, Cantoni, C., C. Bottino, M. Vitale, A. Pessino, R. Augugliaro, A. Malaspina, S. Parolini, L. Moretta, A. Moretta, and R. Biassoni 1999. NKp44, a triggering receptor involved in tumor cell lysis by activated human Natural Killer cells, is a novel member of the immunoglobulin superfamily. J. Exp. Med. 189:787–796).

The library screening procedure was as described (Pessino, A., S. Sivori, C. Bottino, A. Malaspina, L. Morelli, L. Moretta, R. Biassoni, and A. Moretta. 1998. Molecular cloning of NKp46: a novel member of the immunoglobulin superfamily involved in triggering of natural cytotoxicity. J. Exp. Med. 188:953–960, Cantoni, C., C. Bottino, M. Vitale, A. Pessino, R. Augugliaro, A. Malaspina, S. Parolini, L. Moretta, A. Moretta, and R. Biassoni. 1999. NKp44, a triggering receptor involved in tumor cell lysis by activated human Natural Killer cells, is a novel member of the immunoglobulin superfamily. J. Exp. Med. 189:787–796, Brakenhoff, R.H., M. Gerretsen, E.M.C. Knippels, M. van Dijk, H. van Essen, D.O. Weghuis, R.J. Sinke, G.B. Snow, and G.A.M.S. van Dongen. 1995. The human E48 antigen, Highly homologous to the murine Ly-6 antigen ThB, is a GPI-anchored molecule apparently involved in keratinocyte cell-cell adhesion. J. Cell. Biol. 129:1677–1689). Briefly, cDNA library was transiently transfected in COS-7 cells and selection of positive pools was performed by immunocytochemical staining using the specific anti-NKp30 mAb A76 and sib-selection.

DNA Sequencing

DNA sequencing was performed using d-Rhodamine Terminator Cycle Sequencing Kit and a 377 Applied Biosystems Automatic Sequencer (Perkin Elmer-Applied Biosystems, Foster City, Calif.).

Transient Trasfections

COS-7 cells ($5 \times 10^5$/plate) were transfected with VR1012-NK-A1 (clone 5C) or with the vector alone by the DEAE-dextran or electroporation methods as described (Pende D., R. Biassoni, C. Cantoni, S. Verdiani, M. Falco, C. Di Donato, L. Accame, C. Bottino, A. Moretta, and L. Moretta. 1996. The Natural Killer cell receptor specific for HLA.A allotypes: a novel member of the p58/p70 family of inhibitory receptors that is characterized by three immunoglobulin-like domains and is expressed as a 140 kD disulphide-linked dimer. J. Exp. Med. 184:505–518). After 48 hrs, transfected cells were used for cytofluorimetric analysis.

Analysis of NKp30 Transcript Expression by Northern Blotting

In order to analyze NKp30 transcript expression in different cell lines of hematopoietic origin RNA was size fractionated by denaturing agarose gel electrophoresis and transferred onto a positively charged nylon membrane (NEN). In particular, 10 μg of total RNA prepared using CsCl gradient or 2 μg of Poly A+ RNA prepared using Oligo dT magnetic beads separation (Dynal) was loaded on each lane. Northern blots were performed under high stringency conditions as described (Biassoni, R., S. Ferrini, I. Prigione, A. Moretta, and E. O. Long. 1988. CD3-negative lymphokine-activated cytotoxic cells express the CD3 epsilon-gene. J. Immunol. 140:1685–1689). The NKp30 421 bp cDNA probe (SEQ ID NO: 10) was obtained by PCR amplification performed with 25 pmoles of each primer for 30 cycles (30 sec. at 94° C., 30 sec. at 60° C., 30 sec. at 72° C.), followed by a 7 min. incubation at 72° C. The sequences of the primers are: CAG GGC ATC TCG AGT TTC CGA CAT GGC CTG GAT GCT GTT G (NKp30 up; SEQ ID NO: 8) and GAC TAG GAT CCG CAT GTG TAC CAG CCC CTA GCT GAG GAT G (NKp30 down; SEQ ID NO: 9). The cDNA fragment SEQ ID NO: 10 was $^{32}$P-labeled by random priming (Maniatis, T., E. F. Fritsch & J. Sambrook. 1982. Molecular cloning: A laboratory manual. Cold Spring Harbor Laboratory, Cold Spring Harbor, N.Y.).

RT-PCR Amplification of NKp30 cDNA

Total RNA extracted using RNAzol (Cinna/Biotecx, Houston, Tex.) from polyclonal NK and T cell populations and clones and from different hematopoietic cell lines was reverse transcribed using oligodT priming. Primers used for cDNA amplification of NKp30 (606 bp; SEQ ID NO: 12) were the following: 5' CAG GGC ATC TCG AGT TTC CGA CAT GGC CTG GAT GCT GTT G (NKp30 up; SEQ ID NO: 8) and 5' GAT TTA TTG GGG TCT TTT GAA G (rev primer; SEQ ID NO: 11). Amplification was performed with 25 picomoles of each primer for 30 cycles (30 sec. at 94° C., 30 sec, at 60° C., 30 sec. at 72° C.), followed by a 7 min. incubation at 72° C. The amplification products were subcloned in pCR2.1 by TOPO-TA Cloning kit (Invitrogen, Carlsbad, Calif.), and subsequently sequenced.

Zoo-Blot Analysis

Analysis of cross-species conservation of NKp30 gene was performed using a Zoo-Blot (Clontech, Palo Alto, Calif.). The Southern blot contained genomic DNA from human, Rhesus monkey, Sprague-Dawley rat, BALB/c mouse, dog, cow rabbit, chicken, and *Saccharomyces cerevisiae* yeast. The hybridization probe was the same 421 bp cDNA fragment (SEQ ID NO. 10) used to hybridize the Northern blot. Washes were carried out at low stringency conditions as described (Maniatis, T., E. F. Fritsch & J. Sambrook. 1982. Molecular cloning: A laboratory manual. Cold Spring Harbor Laboratory, Cold Spring Harbor, N.Y.).

RESULTS

Identification of a Novel NK-Specific Triggering Surface Molecule

Mice were immunized with $CD3^-$, $16^+$, $56^+$ NK cell clones or bulk populations. Monoclonal antibodies from different fusions were first selected according to their ability to induce lysis of the FcγR+ P815 target cells in a redirected killing assay using polyclonal NK cell populations or clones as effector cells. Three mAbs A76, AZ20 and Z25 (all of IgG1 isotype) were selected that induced a strong cytolytic activity (FIG. 1A) similar to that elicited by other mAbs specific for known triggering NK receptors including CD16, NKp46 and NKp44 (cytolytic activity increase of more than five times the cytolytic activity observed in the absence of the mAbs with E:T of 1:1). In FIG. 1B, the NK cell cytotoxicity induced by graded amounts of AZ20 mAb is compared to that of isotype matched anti-CD16 or anti-CD56 mAbs. The cytolytic response to AZ20 mAb paralleled that induced by anti-CD16 mAb while anti-CD56 mAb had no effect. Moreover, as shown in FIG. 1C, a sharp [Ca++] intracellular increase was detected in the representative clone 3M16 after stimulation with AZ20 mAb. Notably, [Ca++]i increments induced by this antibody occurred only in the presence of a goat anti-mouse second reagent, allowing efficient cross-linking of the activating receptor.

Analysis of the cell surface distribution of the molecule(s) recognized by A76, AZ20 and Z25 mAbs, performed by indirect immunofluorescence and FACS analysis, revealed reactivity with various activated polyclonal or clonal NK cell populations derived from different donors (see below). These also included the infrequent CD16-negative NK cell clones. On the contrary, no mAb reactivity was detected with PHA-induced polyclonal T cell populations or TCR α/β and γ/δT cell clones (derived from different donors). No reactivity was also detected with EBV-induced B cell lines, monocytic and DC lines, and different hemopoietic and non-hemopoietic tumor cell lines including HL60, U937, Eo/A3, THP-1, Daudi, Jurkat, IGROV and all the various tumor cell lines that were used as target cells.

We recently showed that polyclonal NK cell populations from some donors were characterized by a bimodal distribution of fluorescence intensity of NKp46 molecules ($NKp46^{bright}$, and $NKp46^{dull}$) and that NK clones derived from these individuals expressed a stable $NKp46^{bright}$ or $NKp46^{dull}$ phenotype. Importantly, the cytolytic activity of NK cell clones against NK susceptible target cells strictly correlated with their NKp46 phenotype. We then analyzed the reactivity of the new mAbs on polyclonal NK cell populations and NK cell clones derived from individuals displaying different patterns of NKp46 expression. As shown in FIG. 2A, the polyclonal NK cell population derived from the representative donor AM displayed a homogeneously bright phenotype when stained by either AZ20 or anti-NKp46 mAbs. On the contrary, in the polyclonal NK cells derived from donor CB, staining with the same mAbs resulted in a bimodal distribution of fluorescence. Notably, in donor CB the same pattern of fluorescence intensity was also detectable in fresh purified NK cells (FIG. 2A). Moreover, the analysis of several clones derived from donor CB, revealed that $NKp46^{bright}$ clones were consistently $AZ20^{bright}$, whereas $NKp46^{dull}$ clones always displayed an $AZ20^{dull}$ phenotype (FIG. 2B).

In order to further define the pattern of reactivity of the new mAbs in freshly isolated lymphocytes, PBL derived from different individuals were assessed by double fluorescence analysis using informative mAbs. A representative donor is shown in FIG. 3A: the surface molecule recognized by AZ20 mAb was selectively expressed on $CD56^+$ cells. Moreover most $AZ20^+$ cells co-expressed CD16 molecules. On the other hand, AZ20 mAb did not stain $CD3^+$ T lymphocytes or $HLA-DR^+$ B lymphocytes. It is of note that the $CD56^+$ $AZ20$ cell population detected in this donor also expressed surface CD3 molecules. Therefore, also in freshly derived lymphocytes, the reactivity of AZ20 mAb overlaps with that of anti-NKp46 mAb. A direct comparative analysis of the surface expression of NKp46 and AZ20 mAb-reactive molecules is shown in FIG. 3A. The two molecules were clearly co-expressed by the same cell subset. However, no diagonal distribution could be detected in cells stained by AZ20 and anti-NKp46 mAbs while this type of fluorescence distribution occurred when cells were stained simultaneously by two anti-NKp46 mAbs of different isotype.

Notably, results identical to those described for AZ20 mAb were obtained with A76 and Z25 mAbs. These data suggested that the molecule recognized by the new mAbs may be distinct from NKp46. To directly evaluate this possibility, COS-7 cells transiently transfected with NKp46 cDNA were analyzed for their reactivity with AZ20, A76 and Z25 mAbs. Cell transfectants, while reacting with different anti-NKp46 mAbs, were not stained by AZ20, A76 and Z25 mAbs. A76, AZ20 and Z25 mAbs thus appears as specific for a novel surface molecule that defines all mature human NK cells, but is distinct from NKp46.

In order to analyze the biochemical characteristics of the surface molecules recognized by AZ20, A76 and Z25 mAbs, NK populations were surface labeled with $^{125}I$ or biotin, immunoprecipitated with one or another mAb and analyzed by SDS-PAGE. Under these conditions no specific bands could be detected. Thus, integral membrane proteins were prepared from NK cells to further analyze a possible reactivity of the various mAbs in Western blot. As shown in FIG. 3B, AZ20 mAb specifically reacted with a ~30 kD molecule, thereafter termed NKp30. Under the same conditions, both A76 and Z25 mAbs displayed a poorer reactivity.

Cross-Linking of NKp30 Induce Cytolytic Activity Also in Freshly Derived NK Cells Since NKp30 molecule was expressed on fresh NK cells, we analyzed whether it could trigger the cytolytic activity of these cells. As shown in FIG. 4A, AZ20, A76 and Z25 mAbs induced a strong increase of cytolytic activity against P815 target cells while the isotype matched anti-CD56 mAb had no effect. This triggering effect was comparable to that obtained with anti-NKp46 mAb. Moreover, in these experiments, the use of AZ20 F(ab')2 fragments did not induce triggering of cytolytic activity indicating that mAb-dependent NKp30 stimulation requires efficient cross-linking mediated by FcγR on target cells.

Involvement of NKp30 in the Induction of Natural Cytotoxicity Against Normal or Tumor Cells Previous data showed that mAb-mediated masking of NKp46 or NKp44 inhibited the non MHC-restricted tumor cell lysis by activated NK cells. Moreover, masking of NKp46 also inhibited the natural cytotoxicity mediated by freshly isolated peripheral blood NK cells. We then evaluated whether masking of NKp30 could affect the cytolytic activity mediated by freshly derived NK cells or NK clones against a panel of FcγR-negative tumor target cells. As shown in FIG. 4B, anti NKp30 mAb, but not the isotype matched anti-CD56 mAb, inhibited natural cytotoxicity mediated by fresh NK cells against the HLA class I negative 1174 mel, AUMA and FO-1 melanoma cell lines. In addition a greater inhibitory effect occurred when anti-NKp30 mAb was used in combination with anti-NKp46 mAb. NKp30 and NKp46 thus represent receptors that act synergistically in triggering the natural cytotoxicity of fresh NK cells.

In view of these data, the effect of mAb-mediated masking of NKp30 on the tumor cell killing by activated NK cells was further analyzed. FIG. 5 shows three representative NK cell clones analyzed in a cytolytic assay against different tumor targets including two melanomas (MEL15 and M14), an hepatocarcinoma (SMMC) and a lung adenocarcinoma (A549). In previous studies, we showed that the cytolytic activity against the M14 melanoma was confined to NK clones displaying the NKp46$^{bright}$ phenotype and could be inhibited by mAb-mediated masking of NKp46 receptor. On the other hand, NKp46$^{bright}$ clones also killed MEL15, however, neither masking of NKp46 nor of NKp44 significantly inhibited their cytolytic activity. As illustrated above, NKp30 is brightly expressed in NKp46$^{bright}$ clones; therefore it is conceivable that it may play a role in killing of MEL15 target cells. Indeed, as shown in FIG. 5, anti-NKp30 mAb sharply inhibited the NK-mediated lysis of MEL15 cells (>50% of inhibition). Anti-NKp46 mAb exerted a minor effect, while an isotype matched anti-CD56 mAb had no effect. On the contrary, lysis of M14 melanoma was inhibited by anti-NKp46 mAb, whereas anti-NKp30 mAb had virtually no effect. Thus, while NKp46 appears as the major receptor involved in lysis of M14, NKp30 plays a central role in killing of MEL15.

Analysis of the same NK clones in cytolytic assays against other tumor target cells such as SMMC and A549 (FIG. 5) revealed a balanced contribution of NKp46 and NKp30 to the induction of cytotoxicity. Indeed, while mAb-mediated masking of NKp46 or NKp30 alone had a moderate inhibitory effect, the simultaneous masking of the two molecules resulted in a significant inhibition. These results indicate that the two receptors may exert a synergetic effect in the induction of cytotoxcity against certain target cells. Further analysis revealed that NKp30 could exert an additive or synergetic effect in the induction of NK-mediated cytotoxicity not only with NKp46 but also with NKp44. FIG. 6A shows the cytolytic activity of the representative NK clone MIL69 against FO-1 or A549 tumor cells. Target cell lysis was only partially inhibited by mAb-mediated masking of NKp30, NKp44 or NKp46 receptors. However, the combined masking of two receptors resulted in a higher inhibitory effect while the simultaneous masking of the three receptors gave the maximal inhibition. Isotype matched anti-CD56 mAb had no inhibitory affect neither when used alone nor in combination with other mAbs. We further analyzed the role of NKp30 alone or in combination with other receptors, in cytolytic assay using PHA-induced T cell blasts as a source of normal target cells. In these experiments, lysis of autologous cells by NK cell clones was obtained by mAb-mediated masking of HLA class I molecules on target cells to disrupt the interaction with the HLA-class I-specific inhibitory receptors expressed on NK cells. Also under these experimental conditions, the mAb-mediated masking of single receptors had only a partial inhibitory effect on cytotoxicity (FIG. 6B). On the other hand, the simultaneous masking of NKp30, NKp46 and NKp44 receptors strongly reduced (or virtually abrogated) target cell lysis (see the representative clones MX361 and P9). These data support the notion that the ligands recognized by these receptors are expressed not only in tumor but also in normal cells.

Finally, we analyzed the possible involvement of NKp30 in the recognition of murine target cells. The mAb-mediated masking of NKp30 had no effect on the lysis of both BW1502 and YAC-1 murine thymoma cells.

Altogether the above data indicate that NKp30 functions as a major receptor involved in the NK mediated cytotoxicity against normal target cells and most but not all tumor cells. In addition, NKp30 may cooperate with NKp46 and NKp44, most likely depending on the expression of specific ligands by the target cell analyzed.

Molecular Cloning of the cDNA Encoding the NKp30 Molecule

In an attempt to identify the cDNA encoding the NKp30 molecule, a cDNA expression library was generated from the mRNA of human polyclonal NK cells (Pessino, A., S. Sivori, C. Bottino, A. Malaspina, L. Morelli, L. Moretta, R. Biassoni, and A. Moretta. 1998. Molecular cloning of NKp46: a novel member of the immunoglobulin superfamily involved in triggering of natural cytotoxicity. *J. Exp. Med.* 188:953–960). COS-7 cells transfected with different cDNA library pools were stained with A76 mAb by an immunocytochemical detection method. A 674 bp cDNA (NKp30 clone 5C, SEQ ID NO: 1) was isolated that contained a single open reading frame (ORF) of 573 bp (coding sequence SEQ NO: 13). Transfection of COS-7 cells with clone 5C cDNA construct resulted in the surface expression of a molecule that was recognized by all the various anti-NKp30 mAbs (FIG. 7A) but not by anti-NKp46 mAbs as assessed by cytofluorimetric analysis. As shown in FIG. 7B, clone 5C ORF encoded a putative 190 amino acid polypeptide (SEQ ID NO: 2), belonging to the immunoglobulin superfamily (lg-SF), characterized by a signal peptide of 18 amino acid (SEQ ID N°3) and by an extracellular region of 120 amino acids (SEQ ID NO: 4) forming an lg-like domain of the V-type. The extracellular portion contains two potential N-linked glycosylation sites and no consensus sequences for O-linked glycosylation. A region rich in hydrophobic amino acids, potentially involved in protein-protein interactions, is connecting the lg V-like domain with the transmembrane region. The 19 amino acid transmembrane region (SEQ ID NO: 5) contains the positively charged amino acid, Arg and the 33 amino acid cytoplasmic portion (SEQ ID NO; 6) lacks typical ITAM consensus sequences. The presence of a charged amino acid in the transmembrane domain is a feature common to other triggering receptors expressed on NK cells. These charged residues are usually thought to be involved in the association with ITAM containing signaling polypeptides.

EMBUGenBank databases searching revealed that the clone 5C cDNA (SEQ ID NO: 1) was 76.8% identical to a previously identified alternatively spliced form of the 1C7 gene (Acc. NO: AF031138). This gene has been mapped on human chromosome 6, in the TNF cluster of MHC gene complex (Nalabolu, S. R., H. Shukla, G. Nallur, S. Parimoo and S. M. Weissman. 1996. Genes in a 220-kb region spanning the TNF cluster in human MHC. *Genomics* 31:215–22). So far however, neither the function nor the surface distribution of the putative product of 1C7 gene could be identified; and no mAb specific to 1C7 was available. Moreover, the 1C7 transcript could not be revealed by Northern blot on different tissues and cell lines. On the other hand, by RT-PCR the 1C7 transcript could be amplified by RNA isolated from spleen (but not from other tissues) or certain lymphoid and myeloid cell lines. These data suggested that 1C7 transcripts could be poorly represented or could be expressed at substantial levels only in a narrow range of cell types. Our present analysis of NKp30 expression by Northern blotting revealed a mRNA of approximately 1 kb in polyclonal NK cell populations and NK cell lines including NKL and NK3.3. On the contrary, consistent with the lack of reactivity with anti-NKp30 mAbs, no NKp30 mRNA could be detected in human monocytes or cell lines of different histotype including U937, Jurkat, HL60 and LCL 721.221 cells (FIG. 8A). In some of these cell lines which were negative for mRNA expression by Northern blot (and for anti-NKp30 mAb surface staining) it has been possible to detect transcripts when analyzed by RT-PCR technique. This finding is likely to reflect a low level of NKp30 transcription resulting in lack of NKp30 surface expression. Moreover, Northern blot analysis of multiple human tissues showed selective expression of NKp30 transcript only in spleen. Altogether these data are consistent with the fact that NKp30 expression is largely NK-specific.

Finally, the human NKp30 cDNA probe hybridized with genomic DNA from monkey, rat, mouse, dog, cow and rabbit. These data support the fact that the NKp30 encoding gene is highly conserved in different species (FIG. 8B).

Biochemical Characterization of the NKp30 Complex

A NKp30-specific antiserum was generated by immunizing rabbits with an N-terminal NKp30 peptide. As shown in FIG. 9A, the antiserum recognized in Western blot a molecule identical to that previously detected by AZ20 mAb. Unlike the AZ20 mAb, the antiserum immunoprecipitates NKp30 molecules from polyclonal NK cell populations labeled with biotin. Thus, a polyclonal NK cell population, treated or not with sodium pervanadate, was immunoprecipitated with the NKp30-specific antiserum and probed with anti-phosphotyrosine mAb. In order to avoid non specific binding of rabbit Immunoglobulin to CD16 molecules, cell lysates were extensively precleared with anti-CD16 mAb. Moreover, in all experiments pre-immune rabbit serum was used as negative control. In these experiments no tyrosine phosphorylation of NKp30 receptor could be detected. On the other hand, NKp30 receptor associated with a molecule that became tyrosine phosphorylated upon sodium pervanadate treatment (FIG. 9B) and co-migrated with the NKp46 associated CD34ζ chain. The identity between the NKp30-associated molecule and CD3ζ polypeptides was directly demonstrated by its reactivity with anti-CD3ζ mAb (FIG. 9B).

Thus, NKp30, similar to other NK triggering receptors including CD16 and NKp46, can transduce activating signals via the association with the ITAM-containing CD3ζ polypeptides. These data are in agreement with the lack of ITAM in the NKp30 cytoplasmic tail and with the presence of a charged residue in its transmembrane portion.

Discussion

In the present study, thanks to the generation of specific mAbs, we identified and characterized NKp30, a novel triggering receptor that plays an important role in the natural cytotoxicity of both resting and activated human NK cells. Similar to NKp46, NKp30 is selectively expressed by all NK cells, both freshly isolated and cultured in IL-2, thus representing an optimal marker for NK cell identification. Although it belongs to the Ig superfamily, NKp30 does not display any substantial homology with previously identified NK receptors.

In many respects NKp30 appeared similar to NKp46. Indeed, their parallel expression on all NK cells (including the rare CD16-cells), the existence, for both molecules, of a high or low density pattern of surface expression together with their similar functional characteristics led to the thought that the surface molecule recognized by the new mAbs could be identical or strictly related to NKp46. However, NKp30 and NKp46 displayed different molecular masses and, functionally, appeared to play a complementary role in the induction of natural cytotoxicity. Moreover, molecular cloning revealed that NKp30 is a protein with very limited homology with NKp46 as the two molecules display only 13% identity and 15% similarity and are encoded by genes located on different chromosomes.

The receptors responsible for the NK cell triggering during natural cytotoxicity and tumor cell lysis have remained elusive until recently. Available data were consistent with the hypothesis of the existence of multiple triggering NK receptors involved in natural cytotoxicity. In this context, we recently identified NKp46 and NKp44, two receptors involved in recognition and lysis of a variety of tumor targets. Both belong to the Ig superfamily but do not display significant identity. They associate to different signal transducing polypeptides (CD3ζFcεRIγ and KARAP/ DAP12, respectively) that become tyrosine phosphorylated upon NK cell activation. NKp46 and NKp44 were shown to co-operate in the process of tumor cell lysis by human NK cells.

However, lysis of certain target cells was only marginally NKp46- and/or NKp44-dependent since mAb-mediated masking of these molecules did not significantly interfere with cytotoxicity. Moreover although clearly NKp46-and/or NKp44-dependent, the cytolytic activity against other tumor cell lines could not be abrogated by mAb-mediated masking of both molecules suggesting again the existence of additional receptor(s) co-operating with NKp46 and NKp44. Indeed, we show here that NKp30 represents a receptor that may co-operate with NKp46 and NKp44 in the induction of cytotoxicity against a variety of target cells. Perhaps, more importantly, NKp30 represents the major receptor in inducing NK-mediated killing of certain tumor target cells the lysis of which is largely NKp46/NKp44 independent (e.g. melanoma of the MEL 15 type). Remarkably, NKp30, similar to NKp46, is also involved in NK cell activation and target cell killing by fresh NK cells.

As discussed above, the surface expression of NKp30 parallels that of NKp46. Indeed, NK cells displaying a NKp46$^{dull}$ or a NKp46$^{bright}$ phenotype, were also characterized by NKp30$^{dull}$ or NKp30$^{bright}$ fluorescence. We previously showed that NK cell clones characterized by a NKp46$^{dull}$ phenotype consistently express low amounts of NKp44. The finding that NK cells express parallel densities of different triggering receptors may explain the existence of NK cell subsets displaying different "natural" cytolytic activity. For example, it was difficult to understand why the cytolytic activity against some target cells (such as MEL15) although largely NKp46-independent, was essentially confined to NK clones expressing the NKp46$^{bright}$ phenotype. These results can now be explained by the finding that only NKp46$^{bright}$ cells express high density of NKp30 receptor. Thus, the previous demonstration of major differences in cytolytic activity of NKp46$^{dull}$ and NKp46$^{bright}$ cells can now be applied also to NK cells displaying different NKp30 phenotypes. Along this line, the cytolytic activity of NKp30$^{dull}$ NK cell clones was markedly reduced as compared to that of NKp30$^{bright}$ clones.

NKp30, similar to NKp46, associates with CD34 ζ that is most likely involved in signaling via the receptor complex. However, CD34ζ does not appear to be necessary for the surface expression of both receptors at least in COS-7 cells. Molecular cloning revealed that NKp30 is the product of 1C7, a gene previously mapped on human chromosome 6 in the HLA class III region (Nalabolu, S. R., H. Shukla, G. Nallur, S. Parimoo and S. M. Weissman. 1996. Genes in a 220-kb region spanning the TNF cluster in human MHC. *Genomics* 31:215–22 ; Neville, M. J. and R. D. Campbell. 1999. A new member of the lg superfamily and a V-ATPase G subunit are among the predicted products of novel genes close to the TNF locus in the human MHC. *J. Immunol.* 162:4745–4754).

However, neither the function nor the cellular distribution of the putative product of IC7 gene was known and no indications existed on its role in natural cytotoxicity. In addition, the analysis of 1C7 transcript expression was limited to RT-PCR while no detection has been possible by Northern blot analysis. It should also be stressed that no correlation between transcript and surface expression could be established due to the lack of specific mAbs. In the present invention, we show that a precise correlation exists between the surface expression of NKp30, as determined by staining with three different mAbs, and mRNA expression, as assessed by Northern blot. On the contrary, the detection of 1C7 transcripts by RT-PCR does not allow predicting the surface expression of the 1C7/NKp30 molecule.

In conclusion, the NKp30 molecule represents a third member of an emerging family of receptors, termed Natural Cytotoxicity Receptors (NCR), that are involved in NK cell triggering upon recognition of non-HLA ligands. These receptors appear to complement each other in the induction of target cell lysis by NK cells. The relative contribution of each receptor is likely to reflect the xpression/density of their specific ligands on target cells. Along this line, it has recently been shown that also CD16 is involved in natural cytotoxicity thus suggesting that in addition to Fc binding and ADCC, CD16 may play a role in the regulation of NK cell function. Besides CD16 and the different NCR, several other surface molecules that can mediate NK cell triggering have been identified in humans and rodents. These include CD2, CD69, CD28, 2B4 and NKR-P1. However, their actual role in natural cytotoxicity has still to be clarified since in most instances these activating structures are not NK-restricted.

Finally, although the identification of different NCR constitutes a major step forward in our understanding of the NK cell physiology, both the nature and the distribution of the NCR natural ligands on target cells remain to be more precisely determined. Based on the available data, it is possible to envisage a novel mechanism of tumor escape consisting in the down-regulation (on tumor cells) of ligand molecules specifically recognized by NK-specific triggering receptors. Thus, the identification of such ligands will allow the analysis of their distribution in normal vs. tumor cells and to define whether a correlation exists between ligand expression and susceptibility to NK-mediated lysis by different tumor cells.

EXAMPLE 2
Preparation of Anti-NKp30 Antibodies

Once given the NKp30 protein sequence SEQ ID NO: 2 as illustrated in the above example 1, anti-NKp30 antibodies can be generated through conventional antibody production procedures. These include immunizing animals such as mice or rat with a NKp30 immunogenic fragment as defined herein. Repeated immunization can be performed. The antibody response can be monitored using various different techniques such as ELISA or flow cytometry to demonstrate the presence in the serum of the immunized animal of immunoglobulins binding the immunogen. When a significant antibody response is detected, the animal is sacrificed so as to generate monoclonal antibodies as described in conventional procedures such as the Köhler and Milstein procedure (Nature 1975, 256:495–497; Antibodies, a laboratory manual, 1988, Harlow and David Lane, Ed. Cold Spring Harbor laboratory), or such as collecting the immune splenocytes and fusing them to an hybridoma cell line (Anderson, 1989, *J. Immunol.* 143:1889).

The delineation of cell subsets stained by the antibody can be achieved by flow cytometry as described above so as to identify those antibody which have the desired capacity to selectively recognize NK cells among a biological sample. Any of the following readouts can be used in bioassays as described in example 1 to further characterize the stimulating capability of the monoclonal antibodies obtained: (i) induction of natural cytotoxicity towards MHC class I negative targets, tumor cells, virally-infected cells, allogeneic cells,(ii) stimulation of cytotoxicity towards antibody-coated target cells, (iii) increases in intracytoplasmic Ca2+ concentration, (iv) induction of tyrosine phosphorylation of intracytoplasmic adaptor/effector molecules such as ZAP70, Syk, LAT, SLP76, Shc, Grb2, phospholipase C-gamma enzymes, phosphatidyl-inositol 3-kinases, (v) phosphorylation of receptor-associated transducing chains KARAP/DAP12 or CD3zeta or FcRgamma, (vi) cytokine secretion such as interferon gamma, tumor necrosis factors, IL5, IL10, chemokines (such as MIP-lalpha), TGFbeta, (vii) up- or down-regulation of NK cell surface molecules, such as CD69 and PEN5 respectively.

Other procedures can be used to generate antibodies which are capable to bind NKp30 immunogenic fragment, and specifically the screening of phage libraries expressing a repertoire of immunoglobulin fragments in an oligomeric form on their surface. This screening can be achieved by panning recombinant NKp30 molecules on a solid phase, contacting a phage suspension with this coated surface, washing the retained bound phages, replicating these phages, and re-iterating several times this screening procedure with a phage construct expressing fewer immunoglobulin fragment on its surface so as to select the fragments displaying the highest affinity towards the immunogenic molecule. The fragments eventually obtained can be tested for their ability to selectively stain NK cells in biological samples, and to compete with any stimulating antibody in any functional assay as described above.

EXAMPLE 3

NK Cell Purification and Activation

Anti-NKp30 reactants such as anti-NKp30 antibodies advantageously show a NK cell specificity appropriate for NK cell purification from complex biological samples such as plasmapheresis or cytapheresis collection samples. The skilled person can settle a variety of cell purification embodiments.

For instance, anti-NKp30 antibodies NKp30 can be covalently grafted to sub-microscopic MACS microbeads from Miltenyi Biotec gmbh (Gladbach, Germany). Then a suspension of one million to 1 billion nucleated cells from the donor's blood obtained by cytapheresis or by elutriation of donor's peripheral blood sample is contacted with the magnetic beads, and applied to a magnetic sorting device such as the MACS cell sorter from Miltenyi. Alternatively, the anti-NKp30 antibodies can be grafted to Dynabeads® particles from Dynal (Oslo, Norway). The donor cell suspension is incubated with the beads, submitted to a magnetic field in a device such as Isolex device from Baxter, and further recovered by incubation with a peptidic molecule permitting the release of the cells by competition with the NKp30 antigen.

Once purified, the positive cells are then to be recovered in an appropriate isotonic medium, and can be infused to the patient at a dose ranging from 0.1 to 100 millions. The cells can also be frozen after the purification step prior to clinical usage. In autologous procedures, the NK cells are obtained from patient's own blood. In this setting, anti-tumor treatment can be achieved by further incubating the purified NK cells with an antibody binding an antigen expressed by a tumor, such as CD20 in case of B-cell lymphoma, and by re-infusing the processed cells to the patient together with the anti-tumor antibody. Alternatively, in a procedure designed to prevent GvHD (Graft versus Host Disease) occurrence in allogeneic transplantation, such as bone marrow transplantation, the NK cells can be purified from the donor's blood and re-infused as such to the recipient.

NKp30 based positive purification of NK cells has indeed the further advantage to allow a simultaneous NK cell activation, under certain circumstances. These circumstances notably include the use of anti-NKp30 reactants in such a density and/or of such a nature that they allow NKp30 molecule cross-linking on NK cells. Typically, such matrix consists of a solid phase coated with a saturating amount of anti-NKp30 antibody, such as hollow fibers, dextran particles or magnetic particles.

With the simultaneous purification-activation method according to the invention, conventional incubation steps for NK cells activation such as incubating the purified NK cells in the presence of interleukines (e.g. IL-2, IL-12, IL-15) are not a necessary step anymore. It has to be understood that such conventional steps can nevertheless be optionally performed: the skilled person can choose to add such a conventional step to the method according to the invention, e.g. for optimization purposes.

Abbv: NK, natural killer; KIR, killer inhibitory receptor; NCR, natural cytotoxicity receptors; ITAM, immunoreceptor tyrosine-based activating motif; SDS-PAGE, sodium dodecyl sulphate-polyacrilamide gel electrophoresis; lg-SF, immunoglobulin superfamily; RT-PCR, reverse transcriptase-polymerase chain reaction; ORF, open reading frame; mAb monoclonal antibody.

In this description, reference is made to various methodologies known to those of skill in the art of immunology, cell biology, molecular biology and pharmacology. Publications and other materials setting forth such known methodologies to which reference is made are incorporated herein by reference in their entireties as though set forth in full.

What is claimed is:

1. A method for stimulation of cytotoxicity by NK cells comprising contacting said NK cells wvith an amount of antibody cffmdve to stimulate the activity of said NK cells, said antibody being produced by the hybridoma having CNCM Registration Number I-2576 and specificely binding to a polypeptide comprising the amino acid sequence of: SEQ ID NO: 4 or SEQ ID NO: 7.

2. The method according to claim 1, wherein said antibody specifically binds to a polypeptide comprising SEQ ID NO: 4.

3. The method according to claim 1, wherein said antibody specifically binds to a polypeptide comprising SEQ ID NO: 7.

4. A method for stimulation of cytotoxicity by NK cells comprising contacting said NK cells with an amount of antibody effective to stimulate the activity of said NK cells, wherein said antibody specifically binds to a polypeptide consisting of SEQ ID NO: 4.

5. A method for stimulation of cytotoxicity by NK cells comprisinc contacting said NK cells with an amount of antibody effective to stimulate the activity of said NK cells, wherein said antibody specifically binds to a polypeptide consisting of SEQ ID NO: 7.

6. A method for stimulation of cytotoxicity by NK cells comprising contacting said NK cells with an amount of an antibody produced by the hybridoma having CNCM Registration Number I-2576, said antibody having the ability to stimulate the cytotoxicity of said NK cells.

7. A method of binding NK cells to antibody comprising contacting said NK cells with a monocolonal antibody produced by hybridoma CNCM Registrati Number I-2576 or an immunoreactive fragment thereof to form an antibody-NK cell immune complex.

8. The method according to claim 7, wherein said antibody or immunoreactive fragment thereof is coupled to a label.

9. The method according to claim 8, wherein said label is a fluorescent label.

10. The method according to claim 9, wherein said antibody or imnunoreactive fragnent thereof is attached to a solid support.

11. The method according to claim 7, wherein said NK cells are contacted with immunoreactive fragment of a monoclonal antibody produced by CNCM Registration Number I-2576.

* * * * *

UNITED STATES PATENT AND TRADEMARK OFFICE
CERTIFICATE OF CORRECTION

| | | |
|---|---|---|
| PATENT NO. | : 6,979,546 B2 | |
| APPLICATION NO. | : 10/036444 | |
| DATED | : December 27, 2005 | |
| INVENTOR(S) | : Alessandro Moretta, Cristina Bottino and Roberto Biassoni | |

It is certified that error appears in the above-identified patent and that said Letters Patent is hereby corrected as shown below:

<u>Column 9,</u>
Line 63, "anti-p44 antibodies" should read -- anti-NKp44 antibodies --.

<u>Column 13,</u>
Line 25, "Fcy" should read -- Fcγ --.

<u>Column 18,</u>
Line 60, "cuvefte" should read -- cuvette --.

<u>Column 22,</u>
Line 35, "AZ20 cell" should read -- AZ20¯ cell --.

<u>Column 25,</u>
Line 7, "EMBUGenBank" should read -- EMBL/GenBank --.
Line 66, "NKp46 associated CD34ζ chain" should read -- NKp46-associated CD3ζ chain --.

<u>Column 26,</u>
Line 43, "(CD3ζFcεRIγ and" should read -- (CD3ζ/FcεRIγ and --.
Line 61, "NKp46/NKp44 independent" should read -- NKp46/NKp44-independent --.

<u>Column 27,</u>
Lines 19 and 21, "CD34 ζ" should read -- CD3ζ --.

<u>Column 37,</u>
Line 22, "NK cells wvith" should read -- NK cells with --.
Line 23, "cffmdve" should read -- effective --.
Line 25, "specificely" should read -- specifically --.

UNITED STATES PATENT AND TRADEMARK OFFICE
CERTIFICATE OF CORRECTION

PATENT NO. : 6,979,546 B2
APPLICATION NO. : 10/036444
DATED : December 27, 2005
INVENTOR(S) : Alessandro Moretta, Cristina Bottino and Roberto Biassoni It is certified that error appears in the above-identified patent and that said Letters Patent is hereby corrected as shown below:

Column 38,
Line 27, "Registrati" should read -- Registration --.
Line 36, "fragnent" should read -- fragment --.

Signed and Sealed this

Twentieth Day of June, 2006

JON W. DUDAS
*Director of the United States Patent and Trademark Office*

SEQUENCE LISTING

<160> NUMBER OF SEQ ID NOS: 13

<210> SEQ ID NO 1
<211> LENGTH: 674
<212> TYPE: DNA
<213> ORGANISM: Human NK cell

<400> SEQUENCE: 1

```
ccttcctcct ccacccagac ctcactgctc agatcccctt cgccaactgg gacatcttcc      60
gacatggcct ggatgctgtt gctcatcttg atcatggtcc atccaggatc ctgtgctctc     120
tgggtgtccc agcccctga  gattcgtacc ctggaaggat cctctgcctt cctgccctgc     180
tccttcaatg ccagccaagg gagactggcc attggctccg tcacgtggtt ccgagatgag     240
gtggttccag ggaaggaggt gaggaatgga accccagagt tcagggccg cctggcccca     300 cttgcttctt cccgtttcct ccatgaccac caggctgagc tgcacatccg ggacgtgcga     360
ggccatgacg ccagcatcta cgtgtgcaga gtggaggtgc tgggccttgg tgtcgggaca     420
gggaatggga ctcggctggt ggtggagaaa gaacatcctc agctagggc  tggtacagtc     480 ctcctccttc gggctggatt ctatgctgtc agctttctct ctgtggccgt gggcagcacc     540
gtctattacc agggcaaatg ccactgtcac atgggaacac actgccactc ctcagatggg     600
ccccgaggrg tgattccaga gcccagatgt ccctagtcct cttcaaaaga ccccaataaa     660
```
tctgccccac cact                                                                              674

<210> SEQ ID NO 2
<211> LENGTH: 190
<212> TYPE: PRT
<213> ORGANISM: Human NK cell

<400> SEQUENCE: 2

Met Ala Trp Met Leu Leu Ile Leu Ile Met Val His Pro Gly Ser
 1               5                  10                  15

Cys Ala Leu Trp Val Ser Gln Pro Pro Glu Ile Arg Thr Leu Glu Gly
                20                  25                  30

Ser Ser Ala Phe Leu Pro Cys Ser Phe Asn Ala Ser Gln Gly Arg Leu
            35                  40                  45

Ala Ile Gly Ser Val Thr Trp Phe Arg Asp Glu Val Val Pro Gly Lys
        50                  55                  60

Glu Val Arg Asn Gly Thr Pro Glu Phe Arg Gly Arg Leu Ala Pro Leu
 65                  70                  75                  80

Ala Ser Ser Arg Phe Leu His Asp His Gln Ala Glu Leu His Ile Arg
                85                  90                  95

Asp Val Arg Gly His Asp Ala Ser Ile Tyr Val Cys Arg Val Glu Val
                100                 105                 110

Leu Gly Leu Gly Val Gly Thr Gly Asn Gly Thr Arg Leu Val Val Glu
            115                 120                 125

Lys Glu His Pro Gln Leu Gly Ala Gly Thr Val Leu Leu Leu Arg Ala
        130                 135                 140

Gly Phe Tyr Ala Val Ser Phe Leu Ser Val Ala Val Gly Ser Thr Val
145                 150                 155                 160

Tyr Tyr Gln Gly Lys Cys His Cys His Met Gly Thr His Cys His Ser
                165                 170                 175

Ser Asp Gly Pro Arg Gly Val Ile Pro Glu Pro Arg Cys Pro
                180                 185                 190

<210> SEQ ID NO 3
<211> LENGTH: 18
<212> TYPE: PRT
<213> ORGANISM: Human NK cell

<400> SEQUENCE: 3

Met Ala Trp Met Leu Leu Ile Leu Ile Met Val His Pro Gly Ser
 1               5                  10                  15

Cys Ala

<210> SEQ ID NO 4
<211> LENGTH: 120
<212> TYPE: PRT
<213> ORGANISM: Human NK cell

<400> SEQUENCE: 4

Leu Trp Val Ser Gln Pro Pro Glu Ile Arg Thr Leu Glu Gly Ser Ser
 1               5                  10                  15

Ala Phe Leu Pro Cys Ser Phe Asn Ala Ser Gln Gly Arg Leu Ala Ile
                20                  25                  30

Gly Ser Val Thr Trp Phe Arg Asp Glu Val Val Pro Gly Lys Glu Val
            35                  40                  45

Arg Asn Gly Thr Pro Glu Phe Arg Gly Arg Leu Ala Pro Leu Ala Ser
        50                  55                  60

```
Ser Arg Phe Leu His Asp His Gln Ala Glu Leu His Ile Arg Asp Val
 65                  70                  75                  80

Arg Gly His Asp Ala Ser Ile Tyr Val Cys Arg Val Glu Val Leu Gly
                 85                  90                  95

Leu Gly Val Gly Thr Gly Asn Gly Thr Arg Leu Val Val Glu Lys Glu
            100                 105                 110

His Pro Gln Leu Gly Ala Gly Thr
        115                 120

<210> SEQ ID NO 5
<211> LENGTH: 19
<212> TYPE: PRT
<213> ORGANISM: Human NK cell

<400> SEQUENCE: 5

Val Leu Leu Leu Arg Ala Gly Phe Tyr Ala Val Ser Phe Leu Ser Val
 1               5                  10                  15

Ala Val Gly

<210> SEQ ID NO 6
<211> LENGTH: 33
<212> TYPE: PRT
<213> ORGANISM: Human NK cell

<400> SEQUENCE: 6

Ser Thr Val Tyr Tyr Gln Gly Lys Cys His Cys His Met Gly Thr His
 1               5                  10                  15

Cys His Ser Ser Asp Gly Pro Arg Gly Val Ile Pro Glu Pro Arg Cys
                 20                  25                  30

Pro

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence:peptide
      derived from natural sequence, useful for antiserum production

<400> SEQUENCE: 7

Trp Val Ser Gln Pro Pro Glu Ile Arg Thr Leu Glu Gly Ser Cys
 1               5                  10                  15

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: up primer
      for NKp30 cDNA probe of for NKp30 cDNA amplification

<400> SEQUENCE: 8
cagggcatct cgagtttccg acatggcctg gatgctgttg                            40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence:down primer
      for NKp30 cDNA probe amplification

<400> SEQUENCE: 9
```

```
gactaggatc cgcatgtgta ccagcccta gctgaggatg                                    40
```

<210> SEQ ID NO 10
<211> LENGTH: 421
<212> TYPE: DNA
<213> ORGANISM: Human NK cell

<400> SEQUENCE: 10

```
ttccgacatg gcctggatgc tgttgctcat cttgatcatg gtccatccag gatcctgtgc            60
tctctgggtg tcccagcccc ctgagattcg taccctggaa ggatcctctg ccttcctgcc           120
ctgctccttc aatgccagcc aagggagact ggccattggc tccgtcacgt ggttccgaga           180
tgaggtggtt ccagggaagg aggtgaggaa tggaaccccca gagttcaggg gccgcctggc          240
cccacttgct tcttcccgtt tcctccatga ccaccaggct gagctgcaca tccgggacgt           300
gcgaggccat gacgccagca tctacgtgtg cagagtggag gtgctgggcc ttggtgtcgg           360
gacagggaat gggactcggc tggtggtgga gaaagaacat cctcagctag ggctggtac            420
a                                                                          421
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:down primer
      for NKp30 cDNA amplification

<400> SEQUENCE: 11

```
gatttattgg ggtcttttga ag                                                    22
```

<210> SEQ ID NO 12
<211> LENGTH: 606
<212> TYPE: DNA
<213> ORGANISM: Human NK cell

<400> SEQUENCE: 12

```
ttccgacatg gcctggatgc tgttgctcat cttgatcatg gtccatccag gatcctgtgc            60
tctctgggtg tcccagcccc ctgagattcg taccctggaa ggatcctctg ccttcctgcc           120
ctgctccttc aatgccagcc aagggagact ggccattggc tccgtcacgt ggttccgaga           180
tgaggtggtt ccagggaagg aggtgaggaa tggaaccccca gagttcaggg gccgcctggc          240
cccacttgct tcttcccgtt tcctccatga ccaccaggct gagctgcaca tccgggacgt           300
gcgaggccat gacgccagca tctacgtgtg cagagtggag gtgctgggcc ttggtgtcgg           360
gacagggaat gggactcggc tggtggtgga gaaagaacat cctcagctag ggctggtac            420
agtcctcctc cttcgggctg gattctatgc tgtcagcttt ctctctgtgg ccgtgggcag           480
caccgtctat taccagggca atgccactg tcacatggga acacactgcc actcctcaga           540
tgggccccga ggrgtgattc cagagcccag atgtccctag tcctcttcaa aagacccaa           600
taaatc                                                                     606
```

<210> SEQ ID NO 13
<211> LENGTH: 573
<212> TYPE: DNA
<213> ORGANISM: Human NK cell

<400> SEQUENCE: 13

```
atggcctgga tgctgttgct catcttgatc atggtccatc caggatcctg tgctctctgg           60
```

-continued

| | | | | | |
|---|---|---|---|---|---|
| gtgtcccagc | ccctgagat | tcgtaccctg | gaaggatcct | ctgccttcct | gccctgctcc | 120 |
| ttcaatgcca | gccaagggag | actggccatt | ggctccgtca | cgtggttccg | agatgaggtg | 180 |
| gttccaggga | aggaggtgag | gaatggaacc | ccagagttca | ggggccgcct | ggccccactt | 240 |
| gcttcttccc | gtttcctcca | tgaccaccag | gctgagctgc | acatccggga | cgtgcgaggc | 300 |
| catgacgcca | gcatctacgt | gtgcagagtg | gaggtgctgg | gccttggtgt | cgggacaggg | 360 |
| aatgggactc | ggctggtggt | ggagaaagaa | catcctcagc | tagggctgg | tacagtcctc | 420 |
| ctccttcggg | ctggattcta | tgctgtcagc | tttctctctg | tggccgtggg | cagcaccgtc | 480 |
| tattaccagg | gcaaatgcca | ctgtcacatg | ggaacacact | gccactcctc | agatgggccc | 540 |
| cgaggrgtga | ttccagagcc | cagatgtccc | tag | | | 573 |